United States Patent [19]

Yamabe et al.

[11] 4,166,127
[45] Aug. 28, 1979

[54] BENZO[b,f]THIEPIN DERIVATIVES AND PROCESS FOR PRODUCING THE SAME

[75] Inventors: Shigeru Yamabe, Kobe; Yasuo Fujimoto, Tokyo; Shoji Ryu, Noda; Yoshio Suzuki, Misato; Yoshihiro Tanaka, Soka; Toru Yamanaka; Kiyosato Nyu, both of Misato, all of Japan

[73] Assignee: Nippon Chemiphar Co., Ltd., Tokyo, Japan

[21] Appl. No.: 869,767

[22] Filed: Jan. 16, 1978

Related U.S. Application Data

[62] Division of Ser. No. 689,908, May 25, 1976, Pat. No. 4,101,667.

[30] Foreign Application Priority Data

May 30, 1975 [GB]  United Kingdom ............... 23703/75
Oct. 28, 1975 [JP]  Japan ................................. 50-129490

[51] Int. Cl.$^2$ .................... C07D 337/14; A61K 31/38
[52] U.S. Cl. ................................ 424/275; 260/327 B; 549/12
[58] Field of Search ..................... 260/268 TR, 327 B; 424/250, 275; 544/375

[56] References Cited

U.S. PATENT DOCUMENTS 3,811,026   5/1974   Kaplan et al. .................... 260/327 B Primary Examiner—Jose Tovar
Attorney, Agent, or Firm—Oblon, Fisher, Spivak, McClelland & Maier

[57] ABSTRACT

Novel benzo [b,f] thiepin derivatives possessing strong anti-flammatory action and presenting few adverse reactions, of the formula (I)

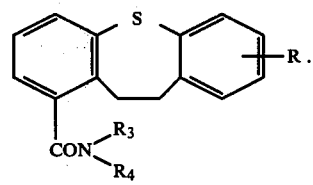

wherein R represents a fluorine atom, or a trifluoromethyl or 1-5C lower alkoxy group, and $R_3$ and $R_4$ each represent a 1-4C lower alkyl group or $R_3$ and $R_4$ together with the adjacent nitrogen atom to which they are attached form a heterocyclic group. Pharmaceutical compositions comprising an anti-inflammatory effective amount of the compound according to formula (I) in the presence of an inert carrier.

5 Claims, No Drawings

BENZO[B,F]THIEPIN DERIVATIVES AND PROCESS FOR PRODUCING THE SAME

This is a division of application Ser. No. 689,908, filed May 25, 1976, now U.S. Pat. No. 4,101,667, issued 7-18-1978.

This invention relates to novel benzo[b,f]thiepin derivatives and to a process for producing the same.

This invention further relates to an intermediate compound which is useful in the preparation of said compounds.

The present inventors have examined a wide variety of benzo[b,f]thiepin type compounds and, as a result, found that benzo[b,f]thiepin derivatives of the formula (I) exhibit an extremely excellent antiinflammatory action:

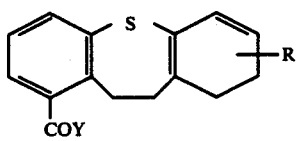

(I)

wherein R represents a hydrogen or fluorine atom, or a trifluoromethyl, 1–5C lower alkoxy, hydroxy, hydroxyethoxy, aminoethoxy group, or the group of the formula —OCH$_2$CH$_2$OCH$_2$CH$_2$OH, Y represents a hydroxy group or the group of the formula

($R_3$ and $R_4$ represent a 1–4C lower alkyl group or $R_3$ and $R_4$ may jointly form a heterocyclic group together with an adjacent nitrogen atom).

It is, therefore, one object of this invention to provide novel benzo[b,f] thiepin derivatives represented by the formula(I).

It is another object of this invention to provide benzo[b,f] thiepin derivatives of the formula (I) possessing a strong antiinflammatory action and presenting fewer adverse reactions.

It is a further object of this invention to provide a novel process for producing benzo[b,f] thiepin derivatives of the formula (I).

It is a further object of this invention to provide an intermediate compound which is useful in the preparation of benzo[b,f] thiepin derivatives of the formula(I).

In the compound of the formula (I), the group represented by R can be substituted at any one of 2-, 3- or 4-position of the benzo[b,f]thiepin ring.

According to the present invention, the benzo[b,f]-thiepin derivatives of the formula (I) are produced according to any one of processes as shown below.
Process 1:

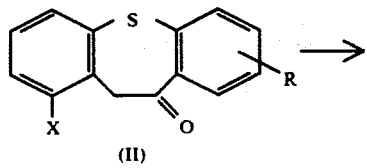

(II)

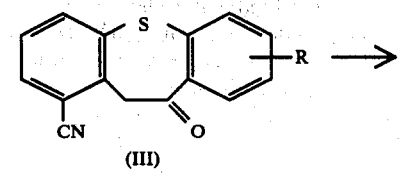

(III)

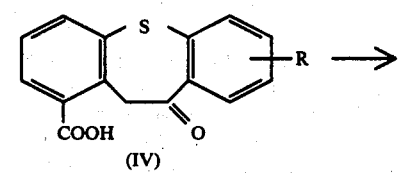

(IV)

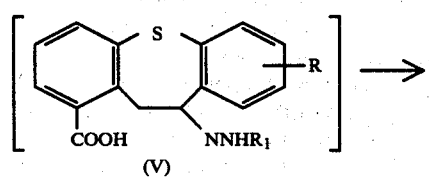

(V)

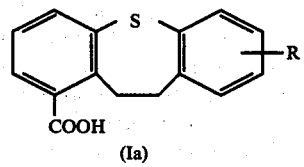

(Ia)

wherein R is as defined above, $R_1$ represents a hydrogen atom or the group of the formula —CONH$_2$ and X represents a bromine or chlorine atom.

According to the present process i, 9-carboxy-10,11-dihydrodibenzo[b,f]thiepin derivatives of the formula (Ia) are produced by → process which comprises reacting 9-halogeno-10,11-dihydro-11-oxo-dibenzo[b,f]thiepin derivatives of the formula(11) with cyanide compounds to produce 9-cyano-10,11-dihydro-11-oxo-dibenzo[b,f]thiepin derivatives of the formula (III), hydrolyzing the compounds (III) to produce 9-carboxy-10,11-dihydro-11-oxo-dibenzo[b,f]thiepin derivatives of the formula (IV), reacting the compounds (IV) with hydrazine or semicarbazide to produce hydrazone or semicarbazone of 9-carboxy-10,11-dihydro-11-oxo-dibenzo[b,f]thiepin derivatives of the formula (V) and then treating the compounds (V) with alkaline reagents.

Suitable cyanide compounds which may be used in the process for producing the compound of the formula (III) from the compound of the formula (II) include metallic cyanides, such as copper cyanide, potassium cyanide and sodium cyanide. The reaction is preferably conducted in N-methylpyrrolidone in view of its solubility, but any solvent which does not participate in the reaction may be used. After the completion of reaction, the compounds of the formula (III) may be isolated from the mixture by usual methods. For example, aqueous ammonia is added to the mixture, which is extracted with organic solvent and the solvent is evaporated to obtain the compounds of the formula (III).

Preferable catalysts to be used in the process for producing the compound of the formula (IV) from the compound of the formula (III) include mineral acids, such as hydrochloric acid and sulfuric acid, and alkaline reagents, such as sodium hydroxide, potassium hydroxide, → metal alkoxide and barium hydroxide. The reaction is preferably conducted in hydrous organic solvents at an elevated temperature. After the completion of reaction, the compounds of the formula (IV) are isolated from the mixture by usual methods. For example, the reaction mixture is concentrated to obtain the residue, to which is added water and the resulting mixture is washed with ether. The aqueous layer is acidified with hydrochloric acid to separate the compounds of the formula (IV), which is collected by filtration. Or the acidic aqueous layer is extracted with organic solvent and the solvent is evaporated to obtain the compounds of the formula (IV).

In producing the compounds of the formula (V) from the compound of the formula (IV), the compounds of the formula (IV) may be reacted with hydrazine or semicarbazide in the solvent which does not participate in the reaction, for example, alcohols such as methanol and ethanol, and ethers such as dioxane and tetrahydrofuran.

In producing the compounds of the formula (Ia) from the compounds of the formula (V), the compounds (V) are reacted with alkaline agents in an inert solvent which does not participate in the reaction, for example, alcohols such as ethanol, t-butanol and diethyleneglycol, and ethers such as dioxane and tetrahydrofuran at an elevated temperature. Alkaline agents to be used in this reaction include potassium hydroxide, sodium hydroxide and metallic alkoxide.

During the course of this process, the group of the formula

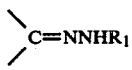

is reduced to the methylene group and at the same time R may be in part converted to a hydroxy group in the case where R stands for a lower alkoxy or fluorine atom, and when this process is conducted in diet yleneglycol, R may be in part converted to the group of the formula —OCH$_2$CH$_2$OCH$_2$CH$_2$OH in the case where R stands for fluorine atom. The compounds of the formula (Ia) can be obtained directly without the isolation of the compounds of the formula (V).

The compound of the formula (II), the starting material of this process 1, is produced by subjecting 6-halogeno-2-phenylthiophenylacetic acid or reactive derivatives thereof to ring closure reaction, as is shown by the following scheme:

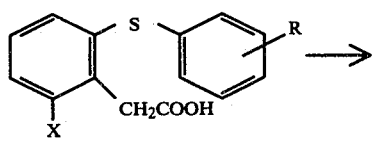

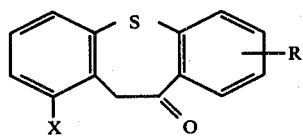

wherein R and X are as defined above.

The reactive derivatives to be used in the above process include acid halides, mixed acid anhydrides, and active esters. The reaction may be preferably conducted in the presence of polyphosphoric acid, polyphosphoric acid ethyl ester, conc. sulfuric acid, hydrogen fluoride, boron fluoride, aluminum chloride, titanium chloride, zinc chloride, tin chloride and trifluoroacetic acid.

Process 2:

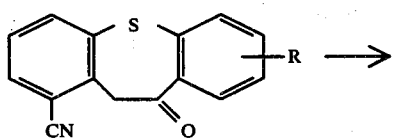

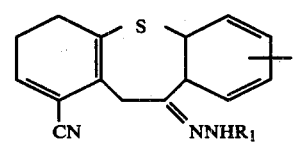

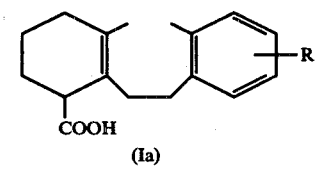

wherein R and R$_1$ are as defined above.

According to the present process 2, 9-carboxy-10,11-dihydrodibenzo[b,f]thiepin derivatives of the formula (Ia) are produced by a process which comprises reacting 9-cyano-10,11-dihydro-11-oxo-dibenzo[b,f]thiepin derivatives of the formula (III) with hydrazine or semicarbazide to produce hydrazone or semicarbazone of 9-cyano-10, 11-dihydro-11-oxo-dibenzo[b,f]thiepin derivatives of the formula (VI) and treating the compounds of the formula (VI) with alkaline reagents.

The present process may be conducted under substantially same condition as in Process 1.

When the compound of the formula (VI) is reacted with alkaline agents, the group of the formula

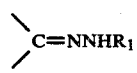

is reduced to a methylene group and at the same time a cyano group is hydrolyzed to a carboxyl group.

Process 3:

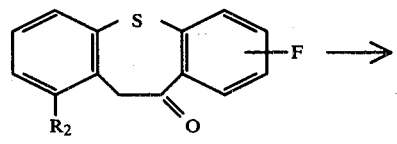

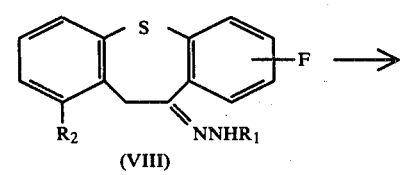

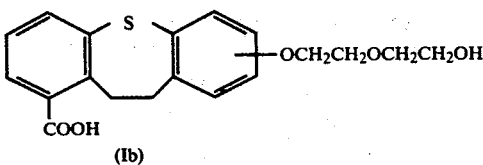

(Ib)

wherein $R_2$ represents a cyano or carboxyl group and $R_1$ is the same as defined above.

According to the present process 3, 9-carboxy-10, 11-dihydrodibenzo[b,f]thiepin derivatives of the formula (Ib) are produced by a process which comprises reacting 9-substituted-10, 11-dihydro-dibenzo[b,f]thiepin-11-one derivatives of the formula (VII) with hydrazine or semicarbazide to produce hydrazone or semicarbazone of 9-substituted-10, 11-dihydrodibenzo[b,f]thiepin-11-one derivatives of the formula (VIII) and treating the compounds of the formula (VIII) with alkaline reagents in the presence of diethylene glycol.

A starting material of the formula (VII) may be easily prepared by reacting the compound of the formula (IX)

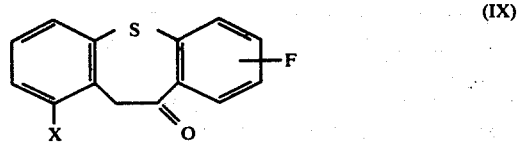

wherein X is as defined above, with metallic cyanides such as copper cyanide, potassium cyanide and sodium cyanide. 9-Carboxy derivatives are produced by hydrolyzing the 9-cyano derivatives obtained as described above.

In producing the compounds of the formula (VIII) from the compounds of the formula (VII) the compounds (VII) are reacted with hydrazine or semicarbazide in an inert organic solvent which does not participate in the reaction, for example, alcohols such as methanol and ethanol, and ethers such as dioxane and tetrahydrofuran. The reaction may be preferably conducted under reflux conditions for 3 to 8 hours.

In producing the compounds of the formula (Ib) from the compounds of the formula (VIII), the compounds of the formula (VIII) are reacted with alkaline agents such as potassium hydroxide, sodium hydroxide and metallic alkoxide in the presence of diethylene glycol at an elevated temperature. During the course of this reaction, the group of the formula

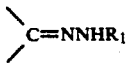

is reduced to a methylene group and at the same time, a cyano group is hydrolyzed to a carboxy group, and a fluorine atom is converted to a diethylene glycoxy group, there is obtained the compound of the formula (Ib).

Process 4:

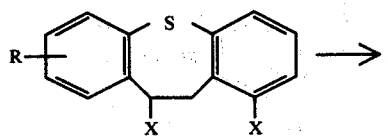

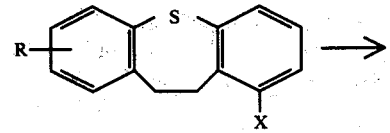

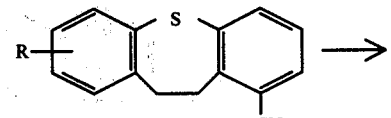

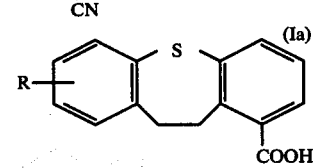

wherein R and X are as defined above.

According to the present process 9-carboxy-10, 11-dihydrodibenzo[b,f]thiepin derivatives of the formula (Ia) are produced by the following process which comprises reducing 9-halogeno-11-halogeno-10, 11-dihydrodibenzo [b,f]thiepin derivatives of the formula (X) to produce 9-halogeno-10, 11-dihydrodibenzo [b,f]thiepin derivatives of the formula (XI), reacting the compounds of the formula (XI) with metallic cyanide compounds, thereby forming 9-cyano-10, 11-dihydrodibenzo[b,f]thiepin derivatives of the formula (XII) and hydrolyzing the compounds of the formula (XII).

In producing the compounds of the formula (XI) from the compounds of the formula (X), the compounds of the formula (X) are subjected to conventional reduction, with the use of reducing agents, such as lithiumaluminum hydride in an inert solvent which does not participate in the reaction and dissolves the compounds of the formula (X) such as tetrahydrofuran for several hours under reflux conditions.

In producing the compounds of the formula (XII) from the compounds of the formula (XI), the compounds of the formula (XI) are reacted with metallic cyanide compounds, such as copper cyanide, sodium cyanide, potassium cyanide and the like. Preferably solvents to be used in this reaction include N-methylpyrrolidone.

In producing the compounds of the formula (Ia) from the compounds of the formula (XII), usual methods are applicable. For example, the compounds of the formula (XII) are heated under reflux conditions in hydrous alcohol containing potassium hydroxide to obtain the compounds of the formula (Ia) in a good yield.

The starting material of the formula (X) is produced by reducing the compound of the formula (II), to obtain 9-halogeno-11-hydroxy-10, 11-dihydro-dibenzo[b,f]thiepin derivatives and halogenating the resulting compound, according to the following scheme.

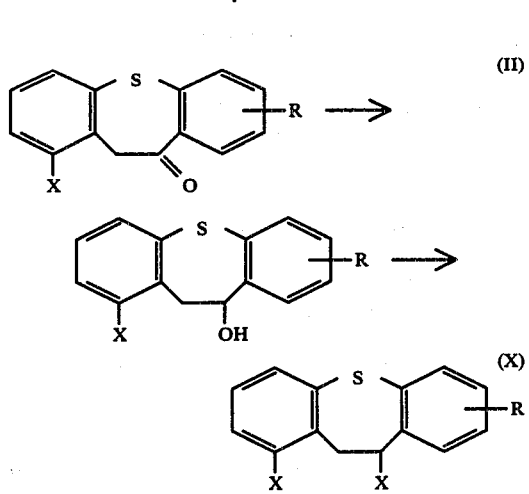

Process 5:

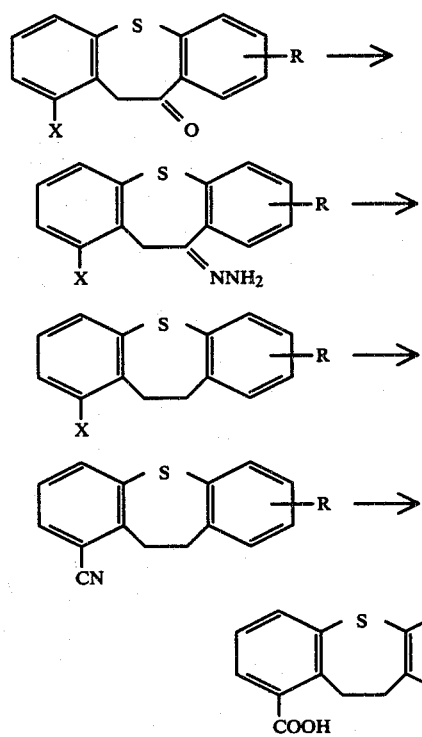

This process can be conducted in a similar manner to the above mentioned.

Process 6:

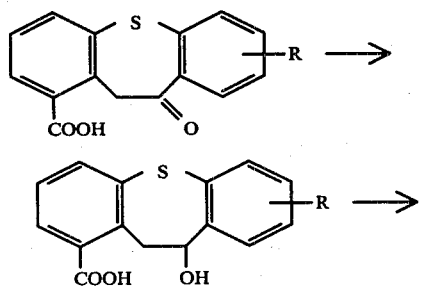

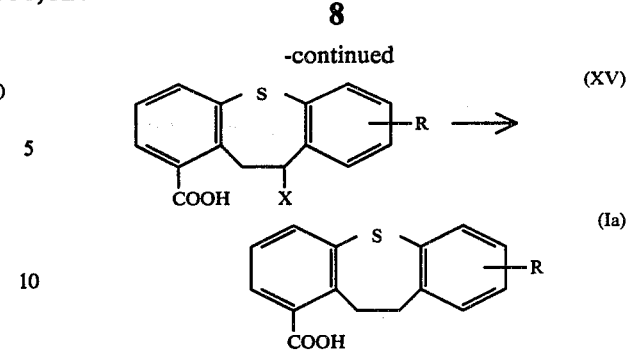

Reduction of a carbonyl group of the compound (IV) in Process 6 can be made by usual methods, preferably with the use of sodium boron hydride. In this case, the reaction proceeds effectively in organic solvents such as alcohols, for example, methanol and ethanol, and ethers, for example, dioxane and tetrahydrofuran at temperature room or an elevated temperature. After the completion of reaction, to the mixture water was added and the resulting mixture was extracted with organic solvent to obtain 9-carboxy-10, 11-dihydrodibenzo[b,f]-thiepin-11-ol derivatives of the formula (XIV).

9-Carboxy-10, 11-dihydro-11-halogenodibenzo[b,f]-thiepin derivatives of the formula (XV) are produced by reacting the compound of the formula (XIV) with a halogenating agent, such as phosphorus trichloride, phosphorus pentachloride, phosphorus oxychloride, thionyl chloride or oxalyl chloride with or without organic solvent which does not participate in the reaction, such as benzene, toluene, hexane and the like.

Reduction of the compound of the formula (XV) may be prefer ably in the presence of catalyst, such as platinum, palladium, nickel, cobalt, iron and copper. The use of lithium aluminum hydride, which may reduce a carboxy group, should be avoided in this reaction.

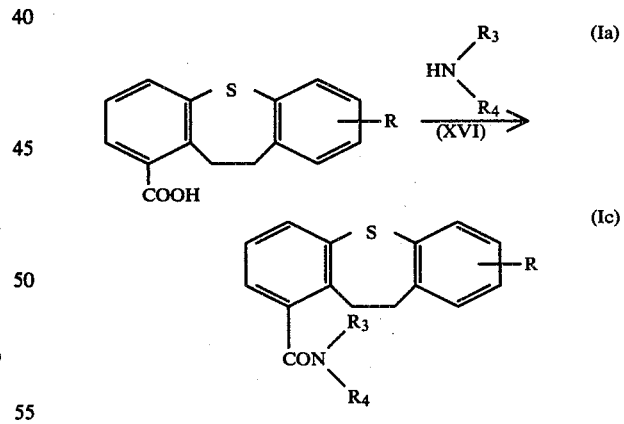

wherein R, $R_3$ and $R_4$ are as defined above.

According to the present process 7, 9-substituted-aminocarbonyl-10, 11-dihydrodibenzo[b,f]thiepin of the formula(Ic) is produced by reacting 9-carboxy-10, 11-dihydrodibenzo[b,f]-thiepin derivatives of the formula (Ia) produced by any one of the above processes, or reactive derivatives thereof, with amino compounds of the formula(XVI).

The active derivatives to be used in this process include acid halides, mixed acid anhydrides and active esters, and the usual methods for producing amides are applicable to this process.

Accordingly, particularly preferred intermediates of benzo[b,f]thiepin derivatives according to the present invention represented by the formula(I) are shown below, which are represented by the formulae (A)-(D).

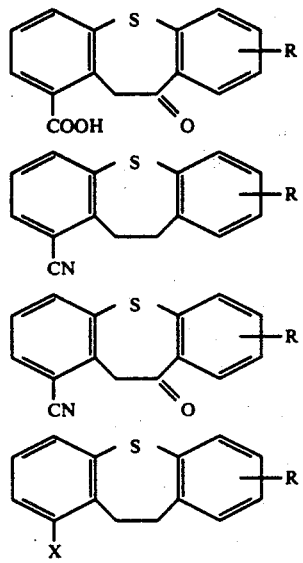

wherein R and X are as defined above.

The compounds of the present invention represented by the formula(I) possess highly excellent antiinflammatory effects.

That is, Wister male rats were given orally the compounds according to the present invention and then induced edema on hind legs by carrageenan injection.

As a result, 30 to 60 percent inhibitory actions were observed at the 2nd hour after oral administration of the present compounds. Significant effects were found even after the 6th hour from the medication.

Wister male rats weighing 120–160 g were used, one group consisting of 5 to 7 rats.

Hind legs were given subcutaneous injections of 0.1 ml of 1% carrageenan at the 1st hour after the medication of 100 mg/kg of the test compounds, and volumes of hind legs were measured by volume differential meter.

The results obtained are shown in Table 1.

Table 1

| Test Compunds | | Maximum Inhibitory Percentage (%) | Maximum Reaction Time (hr.) |
|---|---|---|---|
| Compound | 1 | 38 | 3 |
| " | 2 | 38 | 5 |
| " | 3 | 50 | 5 |
| " | 4 | 32 | 4 |
| " | 5 | 38 | 4 |
| " | 6 | 32 | 5 |
| " | 7 | 41 | 2 |
| " | 8 | 53 | 3 |
| " | 9 | 35 | 2 |
| " | 10 | 40 | 3 |

Compound 1: 2-methoxy-9-carboxy-10,11-dihydrodibenzo[b,f]thiepin 2: 2-methoxy-9-(diisopropylamino) carbonyl-10,11-dihydrodibenzo[b,f]thiepin 3: 2-diethyleneglycoxy-9-carboxy-10,11-dihydrodibenzo[b,f]thiepin 4: 3-diethyleneglycoxy-9-carboxy-10,11-dihydrodibenzo-[b,f]thiepin 5: 3-fluoro-9-carboxy-10,11-dihydrodibenzo[b,f]thiepin 6: 2-fluoro-9-(diisopropylamino) carbonyl-10,11-dihydrodibenzo[b,f]thiepin 7: 2-trifluoromethyl-9-carboxy-10,11-dihydrodibenzo[b,f]-thiepin 8: 2-trifluoromethyl-9-(β-hydroxyethylpiperazinyl)-carbonyl-10,11-dihydrodibenzo[b,f]thiepin hydrochloride 9: 2-(β-hydroxyethoxy)-9-carboxy-10,11-dihydrodibenzo[b,f], thiepin 10: 2-(β-aminoethoxy)-9-carboxy-10,11-dihydrodibenzo[b,f]-thiepin The compound 3,9-carboxy-2-diethyleneglycoxy-10,11-dihydrodibenzo[b,f]thiepin which exerts the most significant effect at the 5th hour after medication as shown in Table 1 was examined for the toxicity thereof in comparison with those of the existing medicaments.

Compound 3, phenylbutazone, flufenamic acid and mefenamic acid were dissolved in 1N—NaOH solution and the resulting solution was adjusted to pH 8–9 with 1N—HCl solution.

100 to 200 mg/kg of each compound was injected intravenously, using dd male mice weighing 20–30 g.

Counting of the number of deaths was performed at the 72nd hour after the administration.

The results obtained are shown in Table 2.

Table 2

| Compounds | | The number of deaths | |
|---|---|---|---|
| | | 100 mg/kg | 200 mg/kg |
| Compound 1 | (a) | 0/5 | 0/5 |
| Phenylbutazone | | 0/5 | 5/5 |
| Flufenamic acid | | 1/5 | 5/5 |
| Mefenamic acid | | 1/5 | 5/5 |

(a) the number of deaths/total number of animals

The invention is illustrated below in further detail with reference to Examples, but the invention is not limited to the Examples.

EXAMPLE 1

2-fluoro-9-chloro-10,11-dihydrodibenzo[b,f]thiepin-11one:

To 1.0 g of 2-chloro-6-(p-fluorophenylthio)phenylacetic acid was added 10 g of polyphosphoric acid and the resulting mixture was stirred at 150° C. for 2 hours. After cooling, to the mixture was added water and the mixture was extracted with benzene. The extract was washed with water, dried over anhydrous sodium sulfate and freed of solvent under reduced pressure. The residue obtained was recrystallized from benzene-n-hexane to afford 0.55 g (58.8%) of 2-fluoro-9-chloro-10,11-dihydrodibenzo[b,f]thiepin-11-one as colorless crystals having a melting point of 135°–137° C.

IR $(\gamma_{max}{}^{KBr}cm^{-1})$: 1660 (C=O).

EXAMPLE 2

2-fluoro-9-chloro-10,11-dihydrodibenzo[b,f]thiepin-11-one:

To 5.9 g of 2-chloro-6-(p-fluorophenylthio)phenylacetic acid was added 60 g of polyphosphoric acid and the resulting mixture was stirred at 150° C. for 2 hours. After cooling, to the mixture was added ice and the thus obtained precipitate was extracted with benzene-diethyl ether. The extract was dried over anhydrous sodium sulfate and freed of solvent by distillation. The residue was washed with diethyl ether-n-hexane, there was obtained 3.5 g (55%) of 2-fluoro-9-chloro-10,11-dihydrodibenzo[b,f]thiepin-11-one as colorless crystals. A part of this product was recrystallized from benzene-n-hexane (3/1) to afford colorless granules having a melting point of 136°–137° C.

Elemental Analysis: as $C_{14}H_8OSClF$; Calculated (%): C: 60.33 H: 2.89; Found (%): C: 60.61 H: 2.86;
IR ($\gamma_{max}^{CHCl_3}$ cm$^{-1}$): 1670 (C=O).
NMR (CDCl$_3$)δ: 4.62 (2H, S, $C_{10}\underline{H_2}$) 7.00-8.00 (6H, m, aromatic protons).

EXAMPLE 3

9-cyano-2-fluoro-10, 11-dihydro-11-oxo-dibenzo[b,f]thiepin:

The mixture of 3.4 g. of 9-chloro-2-fluoro-10, 11-dihydro-11-oxo-dibenzo[b,f]thiepin, 2.1 g of copper cyanide 0.2 g. of anhydrous copper sulfate and 50 ml of N-methyl pyrrolidone was heated at 200°–210° C. overnight. After cooling, to the reaction mixture were added 10 ml of conc. aqueous ammonia and 100 ml of water and the resulting mixture was extracted with benzene. The benzene layer thus obtained was washed with water, dried over anhydrous sodium sulfate and the solvent was distilled off. The resulting residue was chromatographed over silica gel, and eluted with chloroform and benzene. There was obtained from benzene eluate 0.3 g. of 9-cyano-2-fluoro-10,11dihydro-11-oxodibenzo[b,f]thiepin as yellow needles having a melting point of 174°–175° C.

Elemental Analysis: as $C_{15}H_8ONSF$; Calculated (%): C: 66.90 H: 2.99 N: 5.20; Found (%): C: 66.68 H: 2.87 N: 4.94;
IR ($\gamma_{max}^{CHCl_3}$cm$^{-1}$): 218 (CN), 1680 (C=O).
NMR (CDCl$_3$): 4.63 (2H, singlet, $\underline{CH_2}$).
MS (m/e): 269 (M+).

EXAMPLE 4

9-carboxy-2-fluoro-10,11-dihydro-11-oxo-dibenzo[b,f]thiepin:

The mixture of 0.5 g of 9-cyano-2-fluoro-10,11-dihydro-11-oxo-dibenzo[b,f]thiepin, 0.8 g of potassium hydroxide and 5 ml of 90% ethanol was heated overnight under reflux. After the completion of reaction, the reaction mixture was concentrated under reduced pressure and 50 ml of water was added to dissolve the residue which was extracted with diethyl ether. The aqueous layer was acidified with conc. hydrochloric acid to give crystals which were extracted diethyl ether.

The extract was washed with saturated saline solution and dried over anhydrous sodium sulfate. The solvent was distilled off to obtain the residue which was recrystallized from benzene-hexane, and there was obtained 0.5 g of 9-carboxy-2-fluoro-10,11-dihydro-11-oxo-dibenzo[b,f]thiepin as pale yellow granules having a melting point of 242°–244° C.

EXAMPLE 5

9-cyano-2-fluoro-10,11-dihydrobenzo[b,f]thiepin-11-one hydrazone:

The mixture of 0.3 g of 9-cyano-2-fluoro-10,11-dihydrodibenzo[b,f]thiepin-11-one, 0.3 g of 100% hydrazine hydrate and 10 ml of ethanol was heated under reflux on waterbath for 5 hours. The reaction mixture was concentrated to 5 ml to separate crystals on cooling, which was collected by filtration. Recrystallization from ethanol afforded 0.3 g of 9-cyano-2-fluoro-10,11-dihydrodibenzo[b,f]thiepin-11-one hydrazone as pale yellow needles having a melting point of 220°–222° C.

Elemental Analysis: as $C_{15}H_{10}N_3SF$;
Calculated (%): C: 63.59 H: 3.56 N: 14.83; Found (%): C: 63.46 H: 3.47 N: 15.23; IR ($\gamma_{max}^{KBr}$cm$^{-1}$): 3410 (NH$_2$), 2240 (CN); MS (m/e): 283 (M+)

EXAMPLE 6

9-carboxy-2-diethylenegxcoxy-10,11-dihydrodibenzo[b,f]thiepin:

The mixture of 0.3 g of 9-cyano-2-fluoro-10,11-dihydrodibenzo[b,f]thiepin-11-one hydrazone, 0.3 g of sodium hydroxide and 6 ml of diethylene glycol was heated with stirring at 190°–200° C. After cooling, 100 ml of water was added to the reaction mixture, which was extracted with diethyl ether. The aqueous layer was acidified with water to separate crystals, which was extracted with ethyl acetate. The extract was washed with saturated saline solution and dried over anhydrous sodium sulfate. The solvent was evaporated under reduced pressure to obtain the residue, which was chromatographed over silica gel, and eluted with benzene-ethyl acetate (1:1). Recrystallization of the crude product from diethyl ether-petroleum ether afforded 100 mg of 9-carboxy-2-diethyleneglycoxy-10,11-dihydrodibenzo[b,f]thiepin having a melting point of 114°–116° C.

Elemental Analysis: as $C_{19}H_{20}O_5S$ Calculated (%): C: 63.33 H: 5.59; Found (%): C: 63.32 H: 5.66; IR ($\gamma_{max}^{KBr}$ cm$^{-1}$): 1680 (C=O); NMR (CD$_3$OD)δ: 3.22-4.10 (13H, m, methylene protons due to diethylene glycol ether and $C_{10}$, $C_{11}$protons); MS (m/e): 360 (M+).

EXAMPLE 7

2-fluoro-9-(N,N-diisopropyl)aminocarbonyl-10,11-dihydrodibenzo[b,f]thiepin:

An amount of 487.5mg of 2-fluoro-9-carboxy-10,11-dihydrodibenzo[b,f]thiepin was dissolved in 20 ml of anhydrous benzene and to the resulting mixture was added dropwise 2 ml of thionyl chloride. After dropping, the mixture was refluxed for about 5 hours and freed of solvent under reduced pressure. The thus obtained residue was dissolved in 20 ml of anhydrous benzene and to the mixture was added 2.5 ml of diisopropyl amine. The mixture was refluxed for about 3 hours and freed of solvent under reduced pressure. To this was added water and the mixture was extracted with benzene. The extract was washed with water, dried over anhydrous sodium sulfate and freed of solvent under reduced pressure to obtain 190 mg of pale yellow residue. This was recrystallized from n-hexane to give 144 mg (22%) of 2-fluoro-9-(N,N-diisopropyl)aminocarbonyl-10,11-dihydrodibenzo[b,f]thiepin as colorless crystals having a melting point of 149°–150.5° C.

IR ($\gamma_{max}^{KBr}$ cm$^{-1}$): 1620 (C=O)
MS (m/e): 357 (M+).

EXAMPLE 8

9-cyano-2-methoxy-10,11-dihydro-11-oxo-dibenzo[b,f]thiepin:

To 50 ml of N-methylpyrrolidone were added 5.8 g of 9-fluoro-2-methoxy-10,11-dihydro-11-oxo-dibenzo[b,f]-thiepin, 5.4 g of copper cyanide and 0.2 g anhydrous copper sulfate, and the resulting mixture was heated with stirring at 230°–240° C. for 14 hours. After cooling, to the reaction mixture were added 200 ml of 28% aqueous ammonia and 320 ml of water, and the resulting mixture was extracted with benzene. The aqueous and benzene layers were filtered through celite. The collected benzene layer was washed with water several times, diluted hydrochloric acid and then water, which was dried over anhydrous sodium sulfate. The solvent was evaporated to obtain about 6 g of residue which was chromatographed on silice gel. 1.0 g of the starting material was recovered from benzene/chloroform (1/1) eluate and there was obtained from chloroform eluate 9-cyano-2-methoxy-10,11-dihydro-11-oxo-dibenzo[b,f]-thiepin, which was washed with ethanol to give 2.1 g of pale yellow needles having a melting point of 188°–189° C.

IR (KBr, cm$^{-1}$): 2240 (CN), 1675 (CO); NMR (CDCl$_3$, ppm): 3.80 (3H, S, -OCH$_3$), 4.65 (2H, S, -CH$_2$-), 6.88–7.92 (6H,m, aromatic protons) MS (m/e): 281 (M+).

EXAMPLE 9

9-carboxy-2-methoxy-10,11-dihydrodibenzo[b,f]thiepin-11-one:

To the mixture of 1 ml of water and 600 mg of potassium hydroxide in 9 ml of ethanol was added 200 mg of 9-cyano-2-methoxy-10,11-dihydro-11-oxo-dibenzo[b,f]-thiepin and the resulting mixture was heated under reflux overnight. Water was added to the mixture, which was washed with benzene. Aqueous layer was acidified with hydrochloric acid, extracted with chloroform, washed with water and dried over anhydrous sodium sulfate. The solvent was evaporated therefrom and there was obtained 130 mg of 9-carboxy-2-methoxy-10,11-dihydro-11-oxo-dibenzo[b,f]thiepin having a melting point of 157°–160° C.

IR ($\gamma_{max}^{KBr}$ cm$^{-1}$): 1680 (CO); MS (m/e): 300 (M+).

EXAMPLE 10

9-carboxy-2-methoxy-10,11-dihydrodibenzo[b,f]thiepin and 9-carboxy-2-hydroxy-10,11-dihydrodibenzo[b,f]thiepin:

To the mixed solvent of 16 ml of ethanol and 16 ml of dioxane were added 1.8 g of 9-carboxy-2-methoxy-10,11-dihydro-11-oxo-dibenzo[b,f]thiepin and 2.0 g of hydrazine hydrate and the resulting mixture was heated under reflux for 8 hours. After the completion of reaction, the solvent was distilled off and 1.8 g of sodium hydroxide and 30 ml of diethylene glycol was added to the residue. The thus obtained mixture was heated under reflux at 190°–200° C. for 5 hours. After cooling, water was added to the mixture which was extracted benzene. The aqueous layer was acidified with hydrochloric acid and extracted with benzene. The extract was washed with water, dried and the solvent was distilled off. The thus obtained residue was chromatographed over silica gel, eluted with chloroform-diethylether (10:1), was obtained 0.5 g of 9carboxy-2-methoxy-10,11-dihydrodibenzo[b,f]thiepin as colorless needles having a melting point of 185°–187° C.

Elemental Analysis: as C$_{16}$H$_{14}$O$_3$S; Calculated (%): C: 67.11 H:4.93; Found (%): C: 67.36 H: 5.05.

An eluted with diethyl ether, there was obtained 0.3 g of 9-carboxy-2-hydroxy-10,11-dihydrodibenzo[b,f]thiepin as pale yellow prismatic crystals having a melting point of 210–211° C.

IR ($v_{max}^{KBr}$ 3600-3000 (COOH, OH), 1710-1680 (CO); Elemental Analysis: as C$_{15}$H$_{12}$O$_3$S; Calculated (%): C: 66.16 H:4.4; Found (%): C: 65.95 H: 4.27.

EXAMPLE 11

2-methoxy-9-(N,N-diisopropyl)aminocarbonyl-10,11-dihydrodibenzo[b,f]thiepin:

An amount of 575 mg of 2-methoxy-9-carboxy-10,11-dihydrodibenzo[b,f]thiepin was dissolved in 10 ml of anhydrous benzene and to the mixture was added 1 ml of thionyl chloride. The resulting mixture was refluxed for 3 hours and freed of solvent under reduced pressure to obtain 614 mg of 2-methoxy-10,11-dihydrodibenzo[b,f]thiepin-9-carbonyl chloride.

IR ($\gamma_{max}^{KBr}$ cm$^{-1}$): 1765 (CDCl)

The above chloride was dissolved in 10 ml of anhydrous benzene and to the solution was added 1.0 g of diisopropyl amine. The resulting mixture was refluxed for 6 hours. After cooling, to the mixture was added ethyl acetate and the mixture was washed with saturated sodium chloride solution, dried over anhydrous sodium sulfate and freed of solvent under reduced pressure to obtain 660 mg of pale brown crystals.

This was chromatographed over silica gel, and eluted with chloroform-methanol (10/1), there was obtained 647 mg (87%) of pale brown crystals. This was recrystallized from benzene-n-hexane to afford 317 mg of 2-methoxy-9-(N,N-diisopropyl)-aminocarbonyl-10,11-dihydrodibenzo[b,f]thiepine as colourless prismatic crystals having a melting point of 139°–140° C.

IR ($\gamma_{max}^{KBr}$ cm$^{-1}$): 1635 (CON<).

NMR (CDCl$_3$): 1.0–1.6 (6H, m, CH$_3$×2), 1.59–1.64 (6H, m, CH$_3$×2), 3.1–3.8 (4H, m, —CH$_2$CH$_2$—), 3.74 (2H, s, OCH$_3$), 6.56–6172 (2H, m, aromatic protons), 6.92–7.53 (4H, m, aromatic protons)
MS (m/e): 369 (M+).

EXAMPLE 12

9-cyano-2-methoxy-10,11-dihydrodibenzo[b,f]thiepin-11-hydrazone:

900 mg of 9-cyano-2-methoxy-10,11-dihydro-11-oxo-dibenzo[b,f]thiepin was dissolved in the mixed solvent of 8 ml of ethanol and 8 ml of dioxane. To this was added 1.0 g of 100% hydrazine hydrate and the resulting mixture was refluxed with stirring for 7.5 hours. After the completion of reaction, the solvent was distilled off to obtain the residue, which was washed with a small amount of ethanol, and there was obtained 750 mg of 9-cyano-2-methoxy-10,11-dihydro-11-oxo-dibenzo[b,f]thiepin, hydrazone as colorless needles having a melting point of 186°–187° C.

IR (KBr, cm$^{-1}$): 3360 (NH), 3280 (NH), 2230 (CN).

NMR (CDCl$_3$-DMSO, ppm): 3.20 (1H, broad, NH), 3.65 (3H, s, —OCH$_3$), 4.32 (2H, S, —CH$_2$—), 6.24 (1H, broad, —NH), 6.72 (1H, q, J=10 cps, J=2 cps, aromatic protons) 7.16–7.92 (5H, m, aromatic protons).
MS (m/e): 295 (M+).

EXAMPLE 13

9-carboxy-2-methoxy-10,11-dihydrodibenzo[b,f]thiepin:

600 mg of 9-cyano-2-methoxy-10,11-dihydro-11-oxo-dibenzo[b,f]thiepin hydrazone and 600 mg of sodium hydroxide were added to 10 ml of diethylene glycol and the resulting mixture was heated with stirring at 190°–200° C. for 5 hours. After cooling, water was added to the mixture, which was extracted with benzene. The aqueous layer was acidified with hydrochloric acid and extracted with benzene. The benzene extract was washed with water and dried over anhydrous sodium sulfate. The solvent was evaporated to obtain the residue, which was chromatographed over silica gel and eluted with chloroform-ether (10:1). There was obtained 9-carboxy-2-methoxy-10,11-dihydrodibenzo[b,f]thiepin. Recrystallization from benzene afforded 140 mg of the desired product as colorless needles having a melting point of 185°–187° C.

IR (KBr, cm$^{-1}$): 3200–2600 (COOH), 1685 (CO).

NMR (DMSO, ppm): 3.04–3.36 (2H, broad, —CH$_2$—); 3.36–3.72 (5H, broad, —CH$_2$— and —OCH$_3$—), 6.44–6.70 (2H, m), 6.80–7.60 (5H, m, aromatic protons and —COCH).

MS (m/e): 286 (M$^+$).

As eluted with ether, there was obtained 9-carboxy-2-hydroxy-10,11-dihydrodibenzo[b,f]thiepin. Recrystallization from benzene afforded 100 mg of the desired product as pale yellow prismatic crystals having a melting point of 210°–211° C.

IR (KBr, cm$^{-1}$): 3600–3000 (COOH and OH), 1710–1680 (CO).

NMR (DMSO, ppm): 3.80–3.44 (2H, broad, —CH$_2$—), 3.44–3.80 (2H, broad, —CH$_2$—), 6.40–6.70 (2H, m), 7.00–7.80 (4H, m)

MS (m/e): 272 (M$^+$).

EXAMPLE 14

2-hydroxy-9-ethoxycarbonyl-10,11-dihydrodibenzo[b,f]thiepin:

An amount of 1.7 g of 2-hydroxy-9-carboxy-10,11-dihydrodibenzo[b,f]thiepin was dissolved in 50 ml of anhydrous ethanol and the mixture was refluxed for 3 hours, while hydrogen chloride gas was bubbled into the mixture. The solvent was distilled off to obtain the residue which was dissolved in the mixed solvent of ethyl acetate-benzene. The solution was washed with saturated sodium chloride solution and freed of solvent by distillation to obtain 1.6 g (85%) of 2-hydroxy-9-ethoxycarbonyl-10,11-dihydrodibenzo[b,f]thiepin as brown crystals having a melting point of 125°–129° C.

EXAMPLE 15

2-(β-phthalylamino)ethoxy-9-ethoxycarbonyl-10,11-dihydrodibenzo[b,f]thiepin:

The mixture of 780 mg of 2-hydroxy-9-ethoxycarbonyl-10,11-dihydrodibenzo[b,f]thiepin, 1320 mg of β-phthalylaminoethyl bromide and 250 mg of sodium hydride was gradually heated with stirring and then refluxed at 180°–190° C. for 4 hours. After cooling, the mixture was dissolved in the mixed solvent of ethyl acetate and methanol, washed with saturated sodium chloride solution, dried over anhydrous sodium sulfate and freed of solvent under reduced pressure. The resulting residue was chromatographed over a silica gel, and eluted with chloroform, there was obtained the product. This was recrystallized from benzene-n-hexane to afford 580 mg (47%) of 2-(β-phthalylamino) ethoxy-9-ethoxycarbonyl-10,11-dihydrodibenzo[b,f]thiepin as colorless crystals.

EXAMPLE 16

2-(β-amino)ethoxy-9-ethoxycarbonyl-10,11-dihydrodibenzo[b,f]thiepin:

An amount of 330 mg of 2-(β-phthalylamino) ethoxy-9-ethoxycarbonyl-10,11-dihydrodibenzo[b,f]thiepin was dissolved in ethanol and to the resulting solution was added 1 ml of hydrazine hydrate and the mixture was refluxed for 1 hour. After cooling, the separated substance was filtered off and the filtrate was freed of solvent. The residue was dissolved in ethanol and cooled. The separated substance was filtered off and the filtrate was freed of solvent to obtain the residue, which was dissolved in chloroform and cooled. This solution was filtered and the filtrate was evaporated to obtain 217 mg (92%) of 2-(β-amino) ethoxy-9-ethoxycarbonyl-10,11-dihydrodibenzo[b,f]thiepin as pale yellow crystals.

EXAMPLE 17

2-(β-amino)ethoxy-9-carboxy-10,11-dihydrodibenzo[b,f]thiepin:

An amount of 309 mg of 2-(β-amino)ethoxy-9-ethoxy-carbonyl-10,11-dihydrodibenzo[b,f]thiepin was dissolved in 15 ml of ethanol and to the solution was added 10 ml of 5 N sodium hydroxide solution. The mixture was stirred at room temperature for 2 hours and freed of solvent under reduced pressure to obtain the residue, which was dissolved in water and washed with ethyl acetate. The aqueous layer was acidified with conc. hydrochloric acid and extracted with ethyl acetate-methanol. The extract was washed with saturated sodium chloride solution, dried over anhydrous sodium sulfate and freed of solvent to obtain 90 mg of powder. The aqueous layer was freed of water under reduced pressure at 50° C. to obtain the residue, which was extracted with ethanol. The extract was freed of ethanol under reduced pressure to obtain the residue, which was dissolved in ethanol. This solution was filtered, using elite and the filtrate was freed of solvent to obtain 225 mg of powder.

Both powders were combined, dissolved in hydrous ethanol and adsorbed by 20 ml of Dow Ex-1 (X-4, OH form), which was fully washed with hydrous ethanol. When eluted with 2N—HCl-ethanol (1/1), there was obtained white powder. This was recrystallized from anhydrous ethanol-diethyl ether to afford 81 mg ) of 2-(β-amino)ethoxy-9-carboxy-10,11-dihydrodibenzo[b,f]thiepin as white powder having a melting point of 220°–223° C.

IR ($\gamma_{max}^{KBr}$cm$^{-1}$): 1695 (C=O).

MS (m/e): 315 (M$^+$—HCl).

EXAMPLE 18

2-(β-tetrahydropyranyloxy)ethoxy-9-carboxy-10,11-dihydrodibenzo[b,f]thiepin:

To 6 ml of hexamethylphosphorlylamide was added 164 mg of 2-hydroxy-9-ethoxycarbonyl-10,11-dihydrodibenzo[b,f]thiepin and 82 mg of sodium hydride and the resulting mixture was stirred at room temperature for 2 hours. To the mixture was added 250 mg of 2-(β-bromoethoxy)tetrahydropyran and the mixture was stirred at 130° C. for 19 hours. After cooling, to the mixture was added water and the mixture was extracted with ethyl acetate.

The aqueous layer was acidified with hydrochloric acid, extracted ethyl acetate, and the extract was washed with water, dried over anhydrous sodium sulfate and freed of the solvent under reduced pressure to obtain 200 mg of brown oil. This was chromatographed over silica gel, and eluted with benzene-ethanol (100/1), and there was obtained 112 mg of pale brown oil.

This was recrystallized from benzene-n-hexane to afford 97 mg (44.5%) of 2-(β-tetrahydropyranyloxy)ethoxy-9-carboxy-10,11-dihydrodibenzo[b,f]thiepin as colorless crystals having a melting point of 127°–128.5° C.

NMR (CDCl$_3$)δ: 1.40–1.96 (6H, m, methylene protons), 3.24–4.14 (10H, m, methylene protons), 4.60–4.84 (1H, m, methylene proton), 6.60–8102 (6H, m, aromatic protons).

MS (m/e): 400 (M$^+$).

EXAMPLE 19

2-(β-hydroxy)ethoxy-9-carboxy-10,11-dihydrodibenzo[b,f]thiepin:

To the mixed solvent of 6 ml of conc. hydrochloric acid and 6 ml of water was added 100 mg of 2-(β-tetrahydropyranyloxy)ethoxy-9-carboxy-10,11-dihydrodibenzo[b,f]thiepin and the mixture was stirred at room temperature for 2 hours, made basic was diluted sodium hydroxide solution and washed with benzene. The aqueous layer was acidified with hydrochloric acid and extracted with ethyl acetate. The extract was washed with water, dried over anhydrous sodium sulfate and freed of the solvent under reduced pressure to obtain a pale yellow residue. This was recrystallized from benzene to afford 68 mg of 2-(β-hydroxy)ethoxy-9-carboxy-10,11-dihydrodibenzo[b,f]thiepin as colorless crystals having a melting point of 166°–168° C.

IR ($\gamma_{max}^{KBr}$ cm$^{-1}$): 1680 (C=O).

NMR [(CD$_3$)$_2$CO]δ: 3.20–3.56 (2H, m, methylene protons), 3.60–4.20 (6H, m, methylene protons), 6.56–8.00 (6H, m, aromatic protons).

MS (m/e: 316 (M+), 272 (M+ −44).

EXAMPLE 20

9-chloro-10,11-dihydrodibenzo[b,f]thiepin-11-one:

The mixture of 22 g of 2-chloro-6-phenylthiophenylacetic acid and 220 g of polyphosphoric acid was stirred at 120°–130° C. for 2 hours. After cooling, to the mixture was added ice-water and the mixture was extracted with chloroform. The extract was washed with water, saturated sodium bicarbonate solution, then water, and dried ovr anhydrous sodium sulfate. The solvent was distilled off to obtain a residue, which was recrystallized from diethyl ether to afford 14.5 g. (66%) of 9-chloro-10,11-dihydrodibenzo[b,f]thiepin-11-one as colorless needles having a melting point of 122°–125° C.

Elemental Analysis: as C$_{14}$H$_{19}$OSCl; Calculated (%): C: 64.49 H: 3.48; Found (%): C: 64.66 H: 3.31.

IR ($\gamma_{max}^{CHCl_3}$ cm$^{-1}$): 1680 (C=O)

NMR (CDCl$_3$) δ: 4.62 (2H, s, C$_{10}$-$\underline{H_2}$), 7.00–7.63 (6H, m, aromatic protons), 8.23 (1H, d, J=7.6Hz, J=3.3Hz, C$_1$-$\underline{H}$).

EXAMPLE 21

9-cyano-10,11-oxo-dibenzo[b,f]thiepin:

The mixture of 2.6 g of 9-chloro-10,11-dihydro-11-oxo-dibenzo[b,f]thiepin, 2.0 g. of copper cyanide, 0.1 g of anhydrous copper sulfate and 50 ml of N-methyl pyrrolidone was heated with stirring at 200° C. overnight in a flask equipped with a tube packed with silica gel. After cooling, to the reaction mixture were added 100 ml of conc. aqueous ammonia and 200 ml of water, and the resulting mixture was extracted with benzene. The extract was washed with water, diluted hydrochloric acid and then water, which was dried over potassium sulfate and the solvent was evaporated therefrom. The residue thus obtained was chromatographed on 200 g of silica gel, and eluted with chloroform/methanol (50/1). 0.6 g of the starting material was recovered from a first eluate. Recrystallization of the residue of a second eluate from benzene gave 0.7 g of 9-cyano-10,11-dihydro-11-oxo-dibenzo[b,f]thiepin as pale yellow prismatic crystals having a melting point of 165°–167° C.

Elemental Analysis: as C$_{15}$H$_9$ONS; Calculated (%): C: 71.58 H: 3.60 N: 5.57; Found (%): C: 71.68 H: 3.34 N: 5.35.

IR ($\gamma_{max}^{CHCl_3}$ cm$^{-1}$): 2220 (CN), 1680 (CO);

NMR (CDCl$_3$) δ: 4.64 (2H, singlet, C$_{10}$-$\underline{H_2}$) 7.15–7.82 (7H, multiplet, aromatic protons).

MS (m/e): 251 (M+).

EXAMPLE 22

9-carboxy-10,11-dihydro-11-oxo-dibenzo[b,f]thiepin:

3.5 g of 9-cyano-10,11-dihydro-11-oxo-dibenzo[b,f]thiepin was dissolved in 30 ml of 33% potassium hydroxide solution (80% ethanol) and the resulting mixture was heated overnight under reflux. After the mixture was concentrated, water was added to dissolve the residue which was extracted with diethyl ether. The aqueous layer was acidified with conc. hydrochloric acid, extracted with mixed solvent of diethyl ether-ethyl acetate (1:1), washed with saturated saline solution and dried over anhydrous sodium sulfate. The solvent was evaporated and there was obtained 3.4 g of 9-carboxy-10,11-dihydro-11-oxo-dibenzo[b,f]thiepin as pale yellow needles having a melting point of 230°–232° C.

IR ($\gamma^{KBr}_{max}$ cm$^{-1}$): 1730 (COOH), 1650 (CO).

MS (m/e): 270 (M+).

EXAMPLE 23

9-carboxy-10,11-dihydrodibenzo[b,f]thiepin:

The mixture of 1.0 g of 9-carboxy-10,11-dihydro-11-oxo-dibenzo[b,f]thiepin, 1.0 g of hydrazine hydrate and 30 ml of ethanol was heated under reflux on water bath for 4 hours. The reaction mixture was concentrated to about 15 ml to separate crystals on cooling, which were collected by filtration. They were added to the mixture of 1.0 g of sodium hydroxide and 20 ml of diethylene glycal and the resulting mixture was heated with stirring at 190°–200° C. for 2 hours. After cooling, 300 ml of water was added to the mixture, which was extracted with diethyl ether. The aqueous layer was acidified with conc. hydrochloric acid and extracted with chloroform, and the solvent was evaporated therefrom. The thus obtained residue was chromatographed over silica gel and eluted with benzene-ethyl acetate (1:1), and there was obtained 0.4 g of 9-carboxy-10,11-dihydrodibenzo[b,f]thiepin as yellow prismatic crystals having a melting point of 186°–187° C.

Elemental Analysis: as C$_{15}$H$_{12}$O$_2$S; Calculated (%): C: 70.28 H: 4.72; Found (%): C: 70.40 H: 4.81.

EXAMPLE 24

9-cyano-10,11-dihydrodibenzo[b,f]thiepin-11-hydrazone:

g g. of 9-cyano-10,11-dihydro-11-oxo-dibenzo[b,f]thiepin and 1 g of 100% hydrazine hydrate were dissolved in 10 ml of ethanol and the resulting mixture was heated under reflux for 3.5 hours. The reaction mixture was concentrated to 5 ml to separate crystals on cooling, which were collected by filtration. Recrystallization from ethanol afforded 0.6 g of 9-cyano-10,11-dihydro-11-oxo-dibenzo[b,f]thiepin hydrazone as pale brown prismatic crystals having a melting point of 175°–177° C.

IR ($\gamma_{max}^{KBr}$ cm$^{-1}$): 3390 (NH$_2$), 2205 (CN).

NMR [CDCl$_3$+(CD$_3$)$_2$SO]δ: 4.38 (2H, singlet, C$_{10}$-$\underline{H_2}$) 7.18–7.98 (7H, multiplet, aromatic protons).

MS (m/e): 265 (M+).

EXAMPLE 25

9-carboxy-10,11-dihydrodibenzo[b,f]thiepin:

The mixture of 0.5 g of 9-cyano-10,11-dihydro-11-oxo-dibenzo[b,f]thiepin hydrazone. 0.5 g of sodium hydroxide and 10 ml of diethylene glycol was heated ith stirring at 190°–200° for 5 hours. After cooling, 50 ml of water was added to the mixture, which was extracted with 50 ml of diethyl ether. The aqueous layer was acidified with conc. hydrochloric acid to separate crystals, which were extracted with benzene.

The benzene extract was washed with saturated saline solution, and dried over anhydrous sodium sulfate. The solvent was evaporated under reduced pressure. The thus obtained residue was recrystallized from benzene, and there was obtained 0.4 g of 9-carboxy-10,11-dihydrodibenzo[b,f]thiepin as yellow prismatic crystals having a melting point of 187°–188° C.

Elemental Analysis: as $C_{15}H_{12}O_2S$; Calculated (%): C: 70.28 H: 4.72; Found (%): C: 70.37 H: 4.58.

IR ($\gamma_{max}^{KBr}$ cm$^{-1}$): 1685 (CO).

NMR[CDCl$_3$+(CD$_3$)$_2$SO]δ: 3.26–3.40 (2H, multiplet, C$_{11}$—H$_2$), 3.78–3.89 (2H, multiplet, C$_{10}$—H$_2$), 7.08–7.83 (2H, multiplet, aromatic protons).

MS (m/e): 256 (M+).

EXAMPLE 26

4-fluoro-9-chloro-10,11-dihydrodibenzo[b,f]thiepin-11-one:

The mixture of 2.5 g of 2-chloro-6-(0-fluorophenyl-thio)-phenylacetic acid and 30 g of polyphosphoric acid was stirred at 120° C. for 24 hours. After cooling, to the mixture was added ice-water and the mixture was extracted with chloroform. The extract was washed with water, saturated sodium carbonate, then water, dried over anhydrous sodium sulfate and freed of the solvent under reduced pressure to obtain the residue. This was recrystallized from diethylether to afford 1.99 g (82.6%) of 4-fluoro-9-chloro-10,11-dihydrodibenzo[b,f]thiepin-11-one as colorless needles having a melting point of 128°–130° C.

IR ($\gamma_{max}^{CHCl_3}$ cm$^{-1}$): 1680 (C=O)

NMR (CDCl$_3$)δ: 4.58 (2H, s, CH$_2$), 6.95–7.60 (5H, m, aromatic protons) 7.90 (1H, m, C$_1$—H).

MS (m/e): 278 (M+).

EXAMPLE 27

9-cyano-4-fluoro-10,11-dihydrodibenzo[b,f]thiepin-11-one hydrazone:

The mixture of 0.55 g of 9-cyano-4-fluoro-10,01-dihydrodibenzo[b,f]thiepin-11-one, 0.9 g of 100% hydrazine hydrate and 30 ml of ethanol was heated under reflux on a water-bath for 5 hours. The solvent was evaporated to separate crystals, which were washed with small amount of ethanol, and there was obtained 0.55 g of 9-cyano-4-fluoro-10,11-dihydrodibenzo[b,f]thiepin-11-one hydrazone having a melting point of 203°–206° C.

IR ($\gamma_{max}^{KBr}$ cm$^{-1}$): 3400 (NH$_2$), 3240 (NH$_2$), 2240 (CN).

NMR [in (CD$_3$)$_2$SO]δ: 4.35 (2H, s, C$_{10}$—H$_2$), 6.37 (2H, s, NH$_2$), .80–7.90 (6H, m, aromatic protons).

MS (m/e): 283 (M+).

EXAMPLE 28

9-carboxy-4-hydroxy-10,11-dihydrodibenzo[b,f]thiepin:

500 mg of 9-cyano-4-fluoro-10,11-dihydrodibenzo[b,f]thiepin-11-one hydrazone was dissolved in 5 ml of diethylene glycol and to this mixture was added 500 mg of sodium hydroxide in 5 ml of diethylene glycol. The reaction mixture was heated with stirring at 180°–200° C. for 2 hours. After cooling, 30 ml of water was added to the mixture, which was extracted with benzene. The aqueous layer was acidified with conc. hydrochloric acid, extracted with ethy acetate and the extract was washed with water and dried over anhydrous sodium sulfate. The solvent was evaporated to obtain glutinous residue, which was chromatographed over silica gel and eluted with benzene-ethyl acetate (1:1). Recrystallization from diluted methanol solution of the crude product obtained from a first fraction afforded 80 mg of 9-carboxy-4-hydroxy-10,11-dihydrodibenzo[b,f]thiepin having a melting point of 171°–173° C.

IR ($\gamma_{max}^{KBr}$ cm$^{-1}$): 3400 (OH), 1695 (COOH)

NMR (in CD$_3$OD)δ: 3.35, 3.80 (each 2H, two m, C$_{10}$- and C$_{11}$—H$_2$), 6.60–7.82 (6H, m, aromatic protons).

MS (m/e): 272 (M+).

EXAMPLE 29

9-carboxy-4-diethyleneglycoxy-10,11-dihydrodibenzo[b,f]thiepin:

500 mg of 9-cyano-4-fluoro-10,11-dihydro-dibenzo[b,f]thiepin-11-one hydrazone was dissolved in 5 ml of diethylene glycol and to this solution was added 500 mg of sodium hydroxide in 5 ml of diethylene glycol. The thus obtained mixture was heated with stirring at 180°–200° C. for 2 hours. After cooling, 30 ml of water was added to the mixture, which was extracted with benzene. The aqueous layer was acidified with conc. hydrochloric acid and extracted with ethyl acetate. The extract was washed with water and dried over anhydrous sodium sulfate. The solvent was evaporated to obtain a glutinous residue, which was chromatographed over silica gel, and eluted benzeneethyl acetate (1:1). Recrystallization from ethyl acetate of the crude product obtained from a second fraction afforded 190 mg of 9-carboxy-4-diethylene-glycoxy-10,11-dihydrodibenzo[b,f]thiepin having a melting point of 128°–130° C.

IR ($\gamma_{max}^{KBr}$ cm$^{-1}$): 3390 (OH), 1680 (COOH).

NMR (in CD$_3$OD)δ: 3.60–4.24 (12H, m, ethylenic and C$_{10}$ and C$_{11}$—H$_2$ protons), 6.70–7.94 (6H, m, aromatic protons).

MS (m/e): 360 (M+).

EXAMPLE 30

3-fluoro-9-chloro-10,11-dihydrodibenzo[b,f]thiepin-11-one:

The mixture of 8.0 g of 2-chloro-6-(m-fluoro-phenyl-thio)-phenylacetic acid and 80 g at polyphosphoric acid was stirred at 120°–125° C. for 3 hours. After cooling, to the mixture was added water and the mixture was extracted with chloroform. The extract was washed with 100 ml of 1% sodium hydroxide solution, then water, dried over anhydrous sodium sulfate and freed of the solvent to afford 6.2 g (83%) of 3-fluoro-9-chloro-10,11-dihydrodibenzo[b,f]thiepin-11-one having a melting point of 109°–111° C.

IR ($\gamma_{max}^{KBr}$ cm$^{-1}$): 1665 (C=O).

NMR (CDCl$_3$)δ: 8.18 (1H, dd, J=8.5 Hz and 6.0 Hz, C$_1$—H), 7.60–6.88 (5H, m, aromatic protons), 4.58 (2H, s, CH$_2$).

MS (m/e): 280, 278 (M+)

EXAMPLE 31

9-cyano-3-fluoro-10,11-dihydrodibenzo[b,f]thiepin-11-one hydrazone:

The mixture of 1.0 g of 9-cyano-3-fluoro-10,11-dihydrodibenzo[b,f]thiepin-11-one, 1.1 g of 100% hydrazine hydrate and 16 ml of ethanol was heated under reflux for 4.5 hours. The reaction mixture was concentrated to about one-fifth. After cooling, crystals was collected by filtration, there was obtained 9-cyano-3-fluoro-10,11- dihydrodibenzo[b,f]thiepin-11-one hydrazone having a melting point of 178°–179° C. in quantitative yield.

IR ($\gamma_{max}^{KBr}$ cm$^{-1}$): 3400 (NH$_2$), 3240 (NH$_2$).

NMR [(CD$_3$)$_2$SO]δ: 8.00–6.00 (8H, m, aromatic protons and N$\underline{H_2}$), 4.30 (2H, s, —C$\underline{H_2}$—).

MS (m/e): 283 (M+).

EXAMPLE 32

9-carboxy-3-fluoro-10,11-dihydrodibenzo[b,f]thiepin and 9-carboxy-3-hydroxy-10,11-dihydrodibenzo[b,f]thiepin:

To 1.0 g of sodium hydroxide dissolved in 15 ml of diethylene glycol was added 1.0 g of 9-cyano-3-fluoro-10,11-dihydrodibenzo-[b,f]thiepin-11-one hydrazone and the resulting mixture was heated with stirring at 190°–200° C. for 2 hours. After cooling, water was added to the mixture, which was extracted with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with ethyl acetate-benzene (1:10), and there was obtained the crude product. Recrystallization from methanol afforded 102 mg of 9-carboxy-3-fluoro-10,11-dihydrodibenzo[b,f]thiepin having a melting point of 209°–211° C.

IR $\gamma_{max}^{KBr}$ cm$^{-1}$): 3100–2400 (COOH), 1670 (CO).

NMR [(CD$_3$)$_2$SO]δ: 3.00–4.00 (4H, m, C$\underline{H_2}$), 6.88–7.48 (4H, m, aromatic protons), 7.56–7.84 (2H, m, aromatic protons).

MS (m/e): 274 (M+).

As eluted with ethyl acetate-benzene (1:5), there was obtained 52 mg of 9-carboxy-3-hydroxy-10,11-dihydrodibenzo[b,f]-thiepin having a melting point of 219°–221° C. (decomposition).

The Rf values and IR spectra→of this product are in accord with those of the compound obtained according to Example 14.

EXAMPLE 33

9-carboxy-3-hydroxy-10,11-dihydrodibenzo[b,f]thiepin:

1.0 g of 9-cyano-3-fluoro-10,11-dihydrodibenzo[b,f]-thiepin-11-one hydrazone and 1.0 g of sodium hydroxide were added to 15 ml of diethylene glycol and the resulting mixture was heated with stirring at 190°–200° C. for 5 hours. After cooling, water was added to the mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel and eluted with benzene-ethyl acetate (3:2), and there was obtained crude product. Recrystallization from ethanol-water afforded 180 mg of 9-carboxy-3-hydroxy-10,11-dihydrodibenzo[b,f]thiepin having a melting point of 219°–221° C.

IR ($\gamma_{max}^{KBr}$ cm$^{-1}$): 3400–2880 (COOH and OH), 1690 (CO).

NMR (CD$_3$OD)δ: 7.70 (1H, d, d, J=7.5 Hz and 1.0 Hz, C$_6$—$\underline{H}$ or C$_8$—$\underline{H}$), 7.56 (1H, d, d, J=7.5 Hz, and 1.0 Hz, C$_6$—$\underline{H}$ or C$_8$—$\underline{H}$), 7.12 (1H, t, J=7.5 Hz, C$_7$—$\underline{H}$), 6.84 (1H, d, J=8.0 Hz, C$_1$—$\underline{H}$), 6.76 (1H, d, J=2.5 Hz, C$_4$—$\underline{H}$), 6.54 (1H, d, d, J=8.0 Hz and 2.5 Hz, C$_2$—$\underline{H}$), 3.80–3.64 (2H, m, C$\underline{H_2}$), 3.32–3.08 (2H, m, C$\underline{H_2}$).

MS (m/e): 272 (M+).

EXAMPLE 34

9-carboxy-3-diethyleneglycoxy-10,11-dihydrodibenzo[b,f]thiepin:

To 15 ml of diethylene glycol was added 1.0 g of 9-cyano-3-fluoro-10,11-dihydrodibenzo[b,f]thiepin-11-one hydrazone and 1.0 g of sodium hydroxide and the resulting mixture was heated with stirring at 190°–200° C. for 5 hours. After cooling, water was added to the mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with benzene-ethyl acetate (3:2). Recrystallization from methanol-water of th thus obtained product afforded 160 mg of 9-carboxy-3-diethyleneglycoxy-10,11-dihydrodibenzo[b,f]thiepin having a melting point of 125°–128° C.

IR ($\gamma_{max}^{KBr}$ cm$^{-1}$): 3340 (OH), 3000–2500 (COOH), 1700 (CO).

NMR (CD$_3$OD): 7.60–7.40 (2H, m, C$_6$—$\underline{H}$ and C$_8$—$\underline{H}$), 7.20 (1H, t, J=7.5 Hz, C$_7$—$\underline{H}$), 6.76 (1H, d, J=8.0 Hz, C$_1$—$\underline{H}$), 6.72 (1H, d, J=2.5 Hz, C$_4$—$\underline{H}$), 6.52 (1H, d, d, J=8.0 Hz and 2.5 Hz, C$_2$—$\underline{H}$), 4.04–3.00 (12H, m, CH$_2$).

MS (m/e): 360 (M+).

EXAMPLE 35

9-carboxy-3-diethyleneglycoxy-10,11-dihydrodibenzo[b,f]thiepin:

To 1.0 g of sodium hydroxide dissolved in 15 ml of diethylene glycol was added 1.0 g of 9-cyano-3-fluoro-10,11-dihydrodibenzo[b,f]thiepin-11-one hydrazone and the resulting mixture was heated with stirring at 190°–200° C. After cooling, water was added to the mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with ethyl acetate-benzene (1:5). Recrystallization from methanol-water of the thus obtained product afforded 150 mg of 9-carboxy-3-diethyleneglycoxy-10,11-dihydrodibenzo[b,f]thiepin having a melting point of 125°–128° C.

The Rf values and IR spectra:

Values of Rf and results in IR spectrum of this compound are in accord with those of the compound obtained according to Example 21(b-1).

EXAMPLE 36

9-carboxy-3-fluoro-10,11-dihydrodibenzo[b,f]thiepin and 9-carboxy-3-hydroxy-10,11-dihydrodibenzo[b,f]thiepin 5.0 g of 9-carboxy-3-fluoro-10,11-dihydrodibenzo[b,f]thiepin-11-one and 5.0 g of 100% hydrazine hydrate were dissolved in a mixed solvent of 50 ml of ethanol and 50 ml of dioxane and the resulting mixture was heated under reflux for 7 hours. After the solvent was evaporated under reduced pressure, the residue was washed with ethanol and to this was added 5 g of sodium hydroxide in 150 ml of diethylene glycol.

The thus obtained mixture was heated with stirring at 190°–200° C. for 2 hours. After cooling, water was added to the mixture, which was washed with benzene.

The aqueous layer was acidified with hydrochloric acid and extracted with ethyl acetate. The extract was washed with water and dried over anhydrous sodium sulfate. The solvent was evaporated to obtain the residue, which was chromatographed over silica gel and eluted with ethyl acetate-benzene (1:10), and there was obtained crude product. Recrystallization from methanol afforded 800 mg of 9-carboxy-3-fluoro-10,11-dihydrodibenzo[b,f]thiepin having a melting point of 208°–210° C.

Elemental Analysis: as $C_{15}H_{11}SO_2F$; Calculated (%): C: 65.68 H: 4.04; Found (%): C: 65.87 H: 3.95;

IR ($\gamma_{max}^{KBr}$ cm$^{-1}$): 3100–2400 (COOH), 1670 (CO).

NMR [(CD$_3$)$_2$SO]δ: 3.00–4.00 (4H, m, $CH_2 \times 2$), 6.88–7.48 (4H, m, aromatic protons), 7.56–7.84 (2H, m, aromatic protons).

MS (m/e): 274 (M+).

As eluted with ethyl acetate-benzene (1:5), there was obtained 9-carboxy-3-hydroxy-10,11-dihydrodibenzo[b,f]thiepin, which was recrystallized from ethanol-water to give 400 mg of the desired product having a melting point of 219°–221° C. (decomposition).

Elemental Analysis: as $C_{15}H_{12}SO_3$; Calculated (%): C: 66.29 H: 4.51 Found (%): C: 66.16 H: 4.44.

IR ($\gamma_{max}^{KBr}$ cm$^{-1}$): 3400–2880 (COOH, OH), 1690 (CO)

NMR (CD$_3$OD)δ: 3.08–3.32 (2H, m, $\underline{CH_2}$), 3.64–3.80 (2H, m, $\underline{CH_2}$), 6.54 (1H, d, d, J=8 Hz and 2.5 Hz, C$_2$—$\underline{H}$), 6.76 (1H, d, J=2.5 Hz, C$_4$—$\underline{H}$), 6.84 (1H, d, J=8.0 Hz, C$_1$—$\underline{H}$), 7.12 (1H, t, J=7.5 Hz, C$_7$—$\underline{H}$), 7.56 (1H, d, d, J=7.5 Hz and 1.0 Hz, C$_6$—$\underline{H}$ or C$_8$—$\underline{H}$), 7.00 (1H, d, d, J=7.5 Hz and 1.0 Hz, C$_6$—$\underline{H}$ or C$_8$—$\underline{H}$).

MS (m/e): 272 (M+).

EXAMPLE 37

9-carboxy-3-diethyleneglycoxy-10,11-dihydrodibenzo[b,f]-thiepin:

5.0 g of 9-carboxy-3-fluoro-10,11-dihydrodibenzo[b.f]thiepin-11-one and 5.0 g of 100% hydrazine hydrate were dissolved in a mixed solvent of 50 ml of ethanol and 50 ml of dioxane and the resulting mixture was heated under reflux for 7 hours. The solvent was evaporated under reduced pressure to obtain the residue which was washed with ethanol. To this was added 5 g of sodium hydroxide dissolved in 150 ml of diethylene glycol and the resulting mixture was heated with stirring at 190°–200° C. for 2 hours. After cooling, water was added to the reaction mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with ethyl acetate-benzene (1:5). Recrystallization from methanol-water of the thus obtained product afforded 1.2 g of 9-carboxy-3-diethylene-glycoxy-10,11-dihydrodibenzo[b,f]thiepin having a melting point of 125°–128° C.

Elemental Analysis: as $C_{19}H_{20}SO_5$; Calculated (%): C: 63.33 H: 5.59; Found (%): C: 63.58 H: 5.42.

IR ($\gamma_{max}^{KBr}$ cm$^{-1}$): 3340 (OH), 3000–2500 (COOH), 1700 (CO).

NMR (in CD$_3$OD)δ: 3.00–4.04 (12H, m, $\underline{CH_2} \times 6$), 6.52 (1H, d, d, J=8.0 Hz and 2.5 Hz, C$_2$—$\underline{H}$), 6.72 (1H, d, J=2.5 Hz, C$_4$—$\underline{H}$), 6.76 (1H, d, J=8.0 Hz, C$_1$—$\underline{H}$), 7.20 (1H, t, J=7.5 Hz, C$_7$—$\underline{H}$), 7.40–7.60 (2H, m, C$_6$—$\underline{H}$ and C$_8$—$\underline{H}$).

MS (m/e): 360 (M+).

EXAMPLE 38

9-carboxy-4-hydroxy-10,11-dihydrodibenzo[b,f]thiepin:

5.0 g of 9-carboxy-4-fluoro-10,11-dihydrodibenzo[b,f]thiepin-11-one and 5.0 g of 100% hydrazine hydrate were dissolved in the mixed solvent of 50 ml of ethanol and 50 ml of dioxane. The resulting mixture was heated under reflux for 5 hours. The solvent was evaporated under reduced pressure to obtain the residue, which was washed with ethanol. To this was added 5.0 g of sodium hydroxide in 100 ml of diethylene glycol and the resulting mixture was heated with stirring at 180°–200° C. for 2 hours. After cooling, water was added to the mixture, which was extracted with benzene. The aqueous layer was acidified with hydrochloric acid and extracted with ethyl acetate. The extract was washed with water and dried over anhydrous sodium sulfate. The solvent was evaporated to obtain a glutinous residue which was chromatographed over silica gel, and eluted with benzene-ethyl acetate (1:1). Recrystallization of the thus obtained crude product from methanol-water afforded 600 mg of 9-carboxy-4-hydroxy-10,11-dihydrodibenzo-[b,f]thiepin having a melting point of 171°–173° C.

Elemental Analysis: as $C_{15}H_{12}SO_3$; Calculated (%): C: 66.16 H: 4.44; Found (%): C: 66.01 H: 4.39.

IR ($\gamma_{max}^{KBr}$ cm$^{-1}$): 3400 (OH), 1695 (COOH).

NMR (in CD$_3$OD)δ: 3.35, 3.80 (each 2H, two m, C$_{10}$— and C$_{11}$—$\underline{H_2}$), 6.60–7.82 (6H, m, aromatic protons).

MS (m/e): 272 (M+).

EXAMPLE 39

9-carboxy-4-diethyleneglycoxy-10,11-dihydrodibenzo[b,f]-thiepin:

5.0 g of 9-carboxy-4-fluoro-10,11-dihydrodibenzo[b,f]thiepin-11-one and 5.0 g of 100% hydrazine hydrate were dissolved in the mixed solvent of 50 ml of ethanol and 50 ml of dioxane and the resulting mixture was heated under reflux for 5 hours. The solvent was evaporated under reduced pressure to obtain the residue, which was washed with ethanol. To this was added 5.0 g of sodium hydroxide dissolved in 100 ml of diethylene glycol and the resulting mixture was heated with stirring at 180°–200° C. for 2 hours. After cooling, water was added to the mixture, which was extracted with benzene. The aqueous layer was acidified with hydrochloric acid and extracted with ethyl acetate. The extract was washed with water and dried over anhydrous sodium sulfate. The solvent was evaporated to obtain a glutinous residue, which was chromatographed over silica gel, and eluted with benzene-ethyl acetate (1:1). Recrystallization from ethyl acetate of the thus obtained crude product afforded 1.3 g of 9-carboxy-4-diethyleneglycoxy-10,11-dihydrodibenzo[b,f]thiepin having a melting point of 128°–130° C.

Elemental Analysis: as $C_{19}H_{20}SO_5$; Calculated (%): C: 63.33 H: 5.59; Found (%): C: 63.58 H: 5.49.

IR ($\gamma_{max}^{KBr}$ cm$^{-1}$): 3390 (OH), 1680 (COOH).

NMR (in CD$_3$OD)δ: 3.60–4.24 (12H, m, ethylenic protons and C$_{10}$ and C$_{11}$—$\underline{H_2}$), 6.70–7.94 (6H, m, aromatic protons).

MS (m/e): 360 (M+).

EXAMPLE 40

2-trifluoromethyl-9-chloro-10,11-dihydrodibenzo[b,f]thiepin-11-one:

The mixture of 5.6 g of 2-chloro-6-(p-trifluoromethyl-phenylthio)phenylacetic acid and 56 g of polyphosphoric acid was stirred at 130°–140° C. for 4 hours. After cooling, to the mixture was added ice and the mixture was extracted with benzene-ethyl acetate. The extract was washed with water, 2% sodium hydroxide solution, then water, dried over anhydrous sodium sulfate and freed of the solvent under reduced pressure to obtain 1.7 g of crystals. They were chromatographed on silica gel, and eluted with benzene, there was obtained 1.4 g (25.6%) of 2-trifluoromethyl-9-chloro-10,11-dihydrodibenzo[b,f]thiepin-11-on as pale yellow crystals having a melting point of 105°–107.5° C.

IR ($\gamma_{max}^{CHCl_3}$ cm$^{-1}$): 1690 (C=O), 1320 (CF$_3$)
NMR (CDCl$_3$)γ: 4.70 (2H, s,

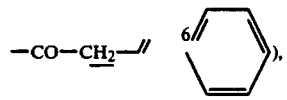

7.10–7.92 (5H, m, aromatic protons), 8.54 (1H, s, aromatic proton).
MS (m/e): 330, 328 (M+).

EXAMPLE 41

2-trifluoromethyl-9-chloro-10,11-dihydrodibenzo[b,f]thiepin-11-ol:

To the mixture of 2-trifluoromethyl-9-chloro-10,11-dihydrodibenzo[b,f]thiepin-11-one obtained in Example 40 and 10 ml of methanol was gradually added 0.2 g of sodium boron hydride with ice-cooling over a period of 5 minutes and the mixture was reacted at room temperature for 30 minutes and refluxed for 15 minutes. After the completion of the reaction, methanol was distilled off. After cooling, to the mixture was added water and the mixture was extracted with chloroform. The extract was washed with water, dried over anhydrous sodium sulfate and freed of the solvent to obtain 0.5 g of 2-trifluoromethyl-9-chloro-10,11-dihydrodibenzo[b,f]thiepin-11-ol as colorless crystals having a melting point of 130°–132° C.

IR ($\gamma_{max}^{CHCl_3}$ cm$^{-1}$): 3600 (OH), disappearance of absorption due to C=O.

NMR (CDCl$_3$)δ: 2.38 (1H, d, O$\underline{H}$), 3.68

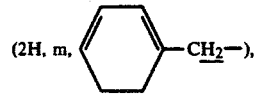

5.50 (1H, d, >C$\underline{H}$—OH),
6.92–7.90 (6H, m, aromatic protons).
MS (m/e): 330, 332 (M+).

EXAMPLE 42

2-trifluoromethyl-9-chloro-11-chloro-10,11-dihydrodibenzo[b,f]thiepin:

To the mixture of 0.5 g of 2-trifluoromethyl-9-chloro-10,11-dihydrodibenzo[b,f]thiepin-11-ol, 5 ml of anhydrous benzene and one drop of anhydrous pyridine were added dropwise with stirring 0.3 g of thionyl chloride with ice-cooling and the resulting mixture was reacted at room temperature for 10 minutes, then refluxed for 20 minutes, and freed of benzene under reduced pressure. To the thus obtained residue was added water and the mixture was extracted with benzene. The extract was washed with water, saturated sodium bicarbonate, then water, dried over anhydrous sodium sulfate and freed of benzene to obtain 2-trifluoromethyl-9-chloro-11-chloro-10,11-dihydrodibenzo[b,f]-thiepin as colorless crystals having a melting point of 88°–90° C.

IR ($\gamma_{max}^{CHCl_3}$ cm$^{-1}$): disappearance of absorption due to OH
NMR (CCl$_4$)δ: 3.94–4.20

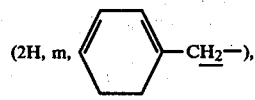

5.68–5.90 (1H, m, >C$\underline{H}$—Cl), 6.96–7.90 (6H, m, aromatic protons).
MS (m/e): 348, 350 (M+).

EXAMPLE 43

2-trifluoromethyl-9-chloro-10,11-dihydrodibenzo[b,f]thiepin:

To the mixture of 0.2 g of lithium aluminum hydride and 20 ml of anydrous tetrahydrofuran was added with stirring under ice-cooling 400 mg of 2-trifluoromethyl-9-chloro-11-chloro-10,11-dihydrodibenzo[b,f]thiepin dissolved in 10 ml of anhydrous tetrahydrofuran. Thereafter, the mixture was reacted under cooling for 0.5 hr. at the room temperature and further under reflux condition for 3.5 hrs. After cooling, to the mixture was added water with stirring under cooling to decompose an excess of lithium aluminum hydroxide and the resulting mixture was filtered with the use of celite. The filtrate was extracted with chloroform, chloroform layer was washed with water and dried over anhydrous sodium sulfate. The solvent was evaporated to obtain 372 ml of an oily substance, which was chromatographed on a silica gel, eluted with n-hexane, and there was obtained 65 mg of 2-trifluoromethyl-9-chloro-10,11-dihydrodibenzo[b,f]thiepin.

NMR (CCl$_4$)δ: 3.20–3.60 (4H, m, methylene protons), 6.90–7.64 (6H, m, aromatic protons).
MS (m/e): 314, 316 (M+).

EXAMPLE 44

2-trifluoromethyl-9-chloro-10,11-dihydrodibenzo[b,f]thiepin-11-hydrazone:

The mixture of 200 mg of 2-trifluoromethyl-9-chloro-10,11-dihydrodibenzo[b,f]thiepin-11-one, 0.8 ml of hydrazine hydrate, 2 ml of ethanol and 2 ml of dioxane was refluxed for 20 hours. After the completion of the reaction, the mixture was freed of the solvent under reduced pressure, and there was obtained 220 mg of 2-trifluoromethyl-9-chloro-10,11-dihydrodibenzo[b,f]thiepin-11-hydrazone as colorless crystals. This was recrystallized from ethanol to give colorless needles having a melting point of 139.5°–141.5° C.

IR ($\gamma_{max}^{CHCl_3}$ cm$^{-1}$): 3420 (NH$_2$).
NMR (CDCl$_3$)δ: 4.28

5.94 (2H, s, N$\underline{H_2}$), 7.00–7.58 (6H, m, aromatic protons), 8.22 (1H, s, aromatic proton).
MS (m/e): 342, 344 (M+).

EXAMPLE 45

2-trifluoromethyl-9-chloro-10,11-dihydrodibenzo[b,f]thiepin:

The mixture of 61 mg of 2-trifluoromethyl-9-chloro-10,11-dihydrodibenzo[b,f]thiepin-11-hydrazone and 2 ml of diethylene glycol was stirred at 180°–200° C. for 2.5 hours. After cooling, to the mixture was added water and the mixture was extracted with chloroform. The mixture was washed with water, dried over anhydrous sodium sulfate and freed of the solvent to obtain 57 mg of a brown oil. This was chromatographed on silica gel and eluted with n-hexane, and there was obtained 2-trifluoromethyl-9-chloro-10,11-dihydrodibenzo[b,f]thiepin.

NMR (CCl$_4$)δ: 3.20–3.60 (4H, m, methylene protons), 6.94–7.64 (6H, m, aromatc protons).

M/S (m/e): 314, 316 (M+).

EXAMPLE 46

2-trifluoromethyl-9-cyano-10,11-dihydrodibenzo[b,f]thiepin:

The mixture of 450 mg of 2-trifluoromethyl-9-chloro-10,11-dihydrodibenzo[b,f]thiepin, 0.4 g of copper cyanide, 0.05 g of anhydrous copper sulfate and 10 ml of N-methylpyrrolidone was stirred at 180° to 210° C. for 18.5 hrs. while preventing the moisture. After cooling, to the mixture was added 2.5 ml of conc. ammonia water and 35 ml of water and the resulting mixture was filtered with the use of celite. The thus obtained solution was extracted with benzene and the extract was washed with water and dried over anhydrous sodium sulfate. The solvent was evaporated to obtain 0.3 g of a brown oily substance, which was chromatographed on a silica gel, eluted with n-hexane, and there was obtained 64 mg of the desired product. This was recrystallized from n-hexane to afford 2-trifluoromethyl-9-cyano-10,11-dihydrodibenzo[b,f]thiepin having a melting point of 113° to 114.5° C. as colorless crystals.

IR ($\gamma_{max}^{CHCl_3}$ cm$^{-1}$): 2230 (CN).

NMR (CCl$_4$)δ: 3.36–3.80 (4H, m, methylene protons), 7.10–7.90 (6H, m, aromatic protons).

MS (m/e): 305 (M+).

EXAMPLE 47

2-trifluoromethyl-10,11-dihydrodibenzo[b,f]thiepin-9-carboxylic acid:

To 1 g of potassium hydroxide dissolved in 1 ml of water and 4 ml of ethanol was added 106 mg of 2-trifluoromethyl-9-cyano-10,11-dihydrodibenzo[b,f]thiepin and the resulting mixture was refluxed for 24 hrs. After cooling, to this was added 4% sodium hydroxide solution and ether. After shaking, the aqueous layer was separated, acidified by adding conc. hydrochloric acid and extracted with chloroform. Extract was washed with water and dried over anhydrous sodium sulfate. The solvent was evaporated to obtain 87 mg (77.3% of yield) of the desired product as colorless powder. This was recrystallized from the mixed solvent of benzene and n-hexane to afford 2-trifluoromethyl-10,11-dihydrodibenzo[b,f]thiepin-9-carboxylic acid having a melting point of 178.5° to 179.5° C. as colorless crystals.

IR ($\gamma_{max}^{KBr}$ cm$^{-1}$): 3400–2400 (COOH), 1680 (CO).

NMR (CDCl$_3$)δ: 3.40–3.60 (2H), 3.84–4.16 (2H, methylene protons), 7.20–8.20 (7H, m, aromatic+—COO$\underline{H}$ protons).

MS (m/e): 324 (M+).

EXAMPLE 48

2-trifluoromethyl-9-(N,N-diisoprophyl)aminocarbonyl-10,11-dihydrodibenzo[b,f]thiepin:

The mixture of 119 mg of 2-trifluoromethyl-9-carboxy-10,11-dihydrodibenzo[b,f]thiepin, 6 ml of anhydrous benzene and 0.2 ml of thionyl chloride was refluxed with stirring for about 5 hours, and then freed of the solvent under reduced pressure. To the residue was added 6 ml of anhydrous benzene and 374 mg of diisopropylamine and the mixture was stirred at room temperature for 15 hours, then refluxed with stirring for 3 hours. Benzene was evaporated and to the residue was added water. The resulting mixture was extracted with chloroform. The extract was washed with water, saturated sodium chloride solution, dried over anhydrous sodium sulfate and freed of the solvent to give 167 mg of the residue. This was chromatographed over silica gel, and eluted with chloroform, there was obtained 38 mg of a colorless glutinous substance.

This was recrystallized from n-hexane, and there was obtained 88 mg (59%) of 2-trifluoromethyl-9-(N,N-diisopropyl)aminocarbonyl-10,11-dihydrodibenzo[b,f]thiepin as colorless crystals having a melting point of 121.5°–122.5° C.

IR ($\gamma_{max}^{KBr}$ cm$^{-1}$): 1620 (C=O)

NMR (CDCl$_3$)δ: 0.92–1.20 (6H, m, C$\underline{H}_3$x2), 1.40–1.52 (6H, m, C$\underline{H}_3$x2), 3.00–3.76 (6H, m, —C$\underline{H}_2$CH$_2$—+C$\underline{H}$x2), 6.84–7.62 (6H, m, aromatic protons).

MS (m/e): 407 (M+).

EXAMPLE 49

2-trifluoromethyl-9-(β-hydroxyethylpiperazinyl)carbonyl-10,11-dihydrodibenzo[b,f]thiepin:

The mixture of 100 mg of 2-trifluoromethyl-9-carboxy-10,11-dihydrodibenzo[b,f]thiepin, 5ml of anhydrous benzene and 0.3 ml of thionyl chloride was refluxed for about 4 hours and, after cooling, freed of the solvent under reduced pressure to obtain the residue. This residue was added to the mixture of 40.5 mg of piperazine ethanol, 31.9 mg of triethylamine and 5 ml of chloroform, and the resulting mixture was stirred at room temperature for about 23 hours. The mixture was extracted with chloroform and the extract was washed with saturated sodium bicarbonate, saturated sodium chloride solution, dried over anhydrous sodium sulfate and freed of chloroform to obtain 18 mg of glutinous substance. This was chromatographed over silica gel and eluted with chloroform, there was obtained 117 mg (87%) of colorless glutinous substance.

This was made hydrochloride and recrystallized from methanol-diethyl ether to give 2-trifluoromethyl-9-(β-hydroxyethylpiperazinyl)carbonyl-10,11-dihydrodibenzo[b,f]thiepin as colorless crystals having a melting point of 248°–250° C.

IR ($\gamma_{max}^{KBr}$ cm$^{-1}$): 3600–3200 (OH), 1620 (C=O).

NMR (CDCl$_3$)δ: 2.24–2.00 (7H, m, methylene protons), 3.80–3.40 (6H, m, methylene protons), 3.48–3.68 (2H, t, J = 6Hz, 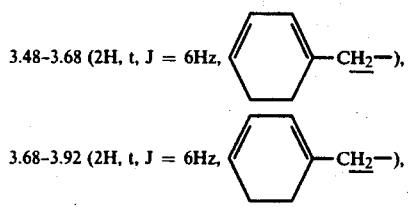

3.68–3.92 (2H, t, J = 6Hz, 7.00–7.52 (6H, m, aromatic protons).
MS (m/e): 436 (M+).

EXAMPLE 50

2-ethoxy-9-chloro-10,11-dihydrodibenzo[b,f]thiepin-11-one:

The mixture of 3 g of 2-chloro-6-(p-ethoxyphenylthio)-phenylacetic acid was stirred at 80°–90° C. After cooling, to the mixture was added 300 g of ice-water and the resulting mixture was extracted with chloroform. The extract was washed with water, 5% sodium bicarbonate solution, then water, dried over anhydrous sodium sulfate and freed of the solvent to give the residue. This residue was recrystallized from benzene-n-hexane to afford 1.2 g (54%) of 2-ethoxy-9-chloro-10,11-dihydrodibenzo[b,f]thiepin-11-one as pale brown powdered crystals having a melting point of 121°–123° C.

IR $(\gamma_{max}^{CHCl_3}$ cm$^{-1})$: 1675 (C=O).
NMR (CDCl$_3$)δ: 1.36 (3H, t, J=7 Hz, C$\underline{H_3}$—CH$_2$), 4.00 (2H, q, J=7 Hz, CH$_3$—C$\underline{H_2}$), 4.62

(2H, s, 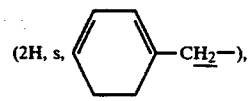

6.80–7.70 (6H, m, aromatic protons).
M/S (m/e) 304 (M+).

EXAMPLE 51

2-ethoxy-9-chloro-10,11-dihydrodibenzo[b,f]thiepin-11-ol:

An amount of 31.8 g of 2-ethoxy-9-chloro-10,11-dihydrodibenzo[b,f]thiepin-11-one was dissolved in 200 ml of a mixed solvent of methanol and chloroform (5/1) and the mixture was stirred at room temperature for 2 hours and freed of the solvent to obtain the residue. To the resulting residue was added 100 ml of water and the mixture was extracted with chloroform. The extract was washed with water, dried over anhydrous sodium sulfate and freed of the solvent to obtain the residue.

This residue was recrystallized from benzene-n-hexane to obtain 1.6 g (89%) of 2-ethoxy-9-chloroform-10,11-dihydrodibenzo[b,f]thiepin-11-ol as colorless powdered cystals having a melting point of 88°–90° C.

IR $(\gamma_{max}^{CHCl_3}$ cm$^{-1})$: 3600 (OH).
MS (m/e): 306 (M+).

EXAMPLE 52

9-chloro-10,11-dihydro-2-ethoxydibenzo[b,f]thiepin:
The mixture of 1.1 g of 9-chloro-10,11-dihydro-2-ethoxy-11-hydroxydibenzo[b,f]thiepin and 35 ml of thionyl chloride was refluxed for 3 hrs. and evaporated to obtain the residue, to which was added 50 g of ice-water. The resulting mixture was extracted with chloroform and the extract was washed with water and dried over calcium chloride. The solvent was evaporated to obtain the concentrated which was added with stirring at room temperature to a mixture of 70 ml of anhydrous tetrahydrofuran and 400 mg of lithium aluminum hydride. The thus obtained mixture was refluxed with stirring for 4 hrs., to which was added 30% sodium hydroxide solution with stirring under cooling with a mixture of ice and sodium chloride. The mixture was filtered and the filtrate was evaporated to obtain the residue, to which was added 100 ml of chloroform and 100 ml of water, and the chloroform layer was collected. This was washed with water, dried and the solvent was evaporated to obtain 520 mg of 9-chloro-10,11-dihydro-2-ethoxydibenzo[b,f]thiepin as oily substance.

NMR (CDCl$_3$)δ: 1.34 (3H, t, J=8 Hz, C$\underline{H_3}$CH$_2$), 3.30 (4H, s, Ar—C$\underline{H_2}$C$\underline{H_2}$—Ar), 3.90 (2H, q, J=8 Hz, CH$_3$C$\underline{H_2}$O), 6.48–7.32 (6H, m, aromatic protons).
MS (m/e): 290 (M+).

EXAMPLE 53

9-cyano-10,11-dihydro-2-ethoxydibenzo[b,f]thiepin:

The mixture of 520 mg of 9-chloro-10,11-dihydro-2-ethoxydibenzo[b,f]thiepin, 0.1 g of copper sulfate, 1 g of copper cyanide and 20 ml of N-methylpyrrolidone was refluxed with stirring for 15 hrs., while preventing the moisture with calcium chloride. After cooling, to this was added 20 ml of conc. ammonia water and 100 ml of water, and the mixture was extracted. The extract was washed with water, dried over anhydrous potassium carbonate and, the solvent was evaporated to obtain the residue. This was chromatographed on silica gel, eluted with the mixed solvent of benzene and n-hexane (4:1) and there was obtained 150 mg of 9-cyano-10,11-dihydro-2-ethoxydibenzo[b,f]thiepin having a melting point of 124° to 126° C. as colorless powdered crystals.

IR $(\gamma_{max}^{CHCl_3}$ cm$^{-1})$: 2230 (CN)
NMR (CDCl$_3$): 1.40 (3H, t, J=7 Hz, C$\underline{H_3}$CH$_2$O), 3.30–3.60 (4H, m, Ar-C$\underline{H_2}$C$\underline{H_2}$-Ar), 4.00 (2H, q, J=7 Hz, CH$_3$C$\underline{H_2}$O), 6.60–7.70 (6H, m, aromatic protons).

EXAMPLE 54

2-ethoxy-10,11-dihydrodibenzo[b,f]thiepin-9-carboxylic acid:

The mixture of 50 mg of 9-cyano-10,11-dihydro-2-ethoxydibenzo[b,f]thiepin, 2 g of potassium hydroxide, 2 ml of water and 10 ml of ethanol was refluxed at 45 hrs., and the solvent was evaporated to obtain a concentrate, which was acidified by adding 10% hydrochloric acid and extracted with chloroform. The extract was washed with water, dried over anhydrous sodium sulfate, and the solvent was evaporated to obtain 45 mg of solid. This was recrystallized from benzene n-hexane to afford 2-ethoxy-10,11-dihydrodibenzo[b,f]thiepin-9-carboxylic acid having a melting point of 165° to 167° C. as colorless powdered crystals.

IR $(\gamma_{max}^{CHCl_3}$ cm$^{-1})$: 1690 (CO). NMR (CDCl$_3$)δ: 1.38 (3H, t, J=7 Hz, CH$_3$C$\underline{H_2}$O), 3.30–3.48 (4H, m, Ar-C$\underline{H_2}$C$\underline{H_2}$-Ar).
MS (m/e): 300 (M+).

EXAMPLE 55

2-methoxy-9-chloro-10,11-dihydrodibenzo[b,f]thiepin-11-one:

The mixture of 30 g of 2-chloro-6-(p-methoxyphenylthio)-phenylacetic acid and 300 g of polyphosphoric acid was stirred at 110° C. for 3 hours. After cooling, to the mixture was added water and the mixture was extracted with chloroform. The extract was washed with 1 N sodium hydroxide solution, saturated sodium chloride solution, dried over anhydrous sodium sulfate and freed of the solvent to afford 22.9 g (81%) of 2-methoxy-9-chloro-10,11-dihydrodibenzo[b,f]thiepin-11-one as reddish crystals having a melting point of 117°–120° C.

IR ($\gamma_{max}^{KBr}$ cm$^{-1}$): 1680 (C=O).

NMR (CDCl$_3$)δ: 3.72 (3H, s, —OC$\underline{H}_3$), 4.56 (2H, s, —C$\underline{H}_2$—), 6.80–7.80 (6H, m, aromatic protons).

EXAMPLE 56

2-methoxy-9-chloro-10,11-dihydrodibenzo[b,f]thiepin-11-hydrazone:

An amount of 20.0 g of 2-methoxy-9-chloro-10,11-dihydrodibenzo[b,f]thiepin-11-one was dissolved in the mixed solvent of 200 ml of ethanol and 200 ml of dioxane and to the mixture was added 30.0 g of hydrazine hydrate.

The resulting mixture was refluxed for 20 hours and, after cooling, freed of the solvent to obtain the residue. This residue was recrystallized from ethanol to afford 12.6 g (60%) of 2-methoxy-9-chloro-10,11-dihydrodibenzo[b,f]thiepin-11-hydrazone as pale yellow crystals having a melting point of 116°–119° C.

IR ($\gamma_{max}^{KBr}$ cm$^{-1}$): 3220, 3340 (NH$_2$).

EXAMPLE 57

2-methoxy-9-chloro-10,11-dihydrodibenzo[b,f]thiepin:

An amount of 12.5 g of sodium hydroxide was dissolved in 250 ml of diethylene glycol by application of heat and to the resulting solution was added 12.5 g of 2-methoxy-9-chloro-10,11-dihydrodibenzo[b,f]thiepin-11-hydrazone and the mixture was stirred at 150° C. for 4 hours. After cooling, to the mixture was added water and the mixture was extracted with ethyl acetate. The extract was washed with saturated sodium chloride solution, dried over anhydrous sodium sulfate and freed of the solvent to obtain 12.0 g of brown oil. This residue was chromatographed over a silica gel and eluted with benzene-n-hexane (1/1) and there was obtained 10.9 g (96%) of 2-methoxy-9-chloro-10,11-dihydrodibenzo[b,f]thiepin as chlorless prismatic crystals having a melting point of 73°–74° C.

NMR (CDCl$_3$)δ: 3.61 (4H, s, —C$\underline{H}_2$C$\underline{H}_2$—), 3.80 (3H, s, OC$\underline{H}_3$), 6.60–7.46 (6H, m, aromatic protons).

EXAMPLE 58

2-methoxy-9-cyano-10,11-dihydrodibenzo[b,f]thiepin:

To 100 ml of N-methylpyrrolidone was added 10.8 g of 2-methoxy-9-chloro-10,11-dihydrodibenzo[b,f]thiepin, 10.7 g of copper cyanide and 0.4 g of anhydrous copper sulfate and the resulting mixture was stirred at 190°–195° C. for 15 hours. After cooling, to the mixture was added 28% ammonia water, 200 ml of water and 200 ml of benzene and the resulting mixture was shaked and filtered with celite. The filtrate was extracted with benzene. The extract was washed with saturated sodium chloride solution, dried over anhydrous sodium sulfate and freed of the solvent to obtain 9.0 g of light brown crystals. This product was chromatographed over silica gel and eluted with benzene, there was obtained 5.4 g (50%) of 2-methoxy-9-cyano-10,11-dihydrodibenzo[b,f]thiepin as colorless prismatic crystals having a melting point of 129°–130° C.

IR ($\gamma_{max}^{KBr}$ cm$^{-1}$): 2215 (CN).

NMR(CDCl$_3$)δ: 3.24–3.54 (4H, m, —C$\underline{H}_2$C$\underline{H}_2$—) 3.73 (3H, s, OC$\underline{H}_3$) 6.50–7.60 (6H, m, aromatic protons).

MS (m/e): 267 (M+).

EXAMPLE 59

2-hydroxy-9-carboxy-10,11-dihydrodibenzo[b,f]thiepin.

An amount of 2.2 g of sodium hydroxide was dissolved in 30 ml of diethylene glycol by application of heat and to the mixture was added 2.2 g of 2-methoxy-9-cyano-10,11-dihydrodibenzo[b,f]thiepin and the resulting mixture was stirred at 200° C. for 16 hours. After cooling, to the mixture was added water and the mixture was extracted with ethyl acetate. The aqueous layer was acidified with conc. hydrochloric acid and extracted with ethyl acetate. This extract was washed with saturated sodium chloride solution, dried over anhydrous sodium sulfate and freed of the solvent to obtain the residue. This residue was recrystallized from benzene to afford 1.1 g (46%) of 2-hydroxy-9-carboxy-10,11-dihydrodibenzo[b,f]thiepin as brown crystals having a melting point of 210°–211° C.

EXAMPLE 60

2-methoxy-9-carboxy-10,11-dihydrodibenzo[b,f]thiepin.

An amount of 6.0 g of potassium hydroxide was dissolved in 20 ml of 80% ethanol and to the solution was added 1 g of 2-methoxy-9-cyano-10,11-dihydrodibenzo[b,f]thiepin and the resulting mixture was refluxed for 26 hours. The mixture was freed of the solvent under reduced pressure to obtain the residue, which was dissolved in water and extracted with ethyl acetate. The aqueous layer was acidified with conc. hydrochloric acid and extracted with ethyl acetate. The extract was washed with saturated sodium chloride solution, dried over anhydrous sodium sulfate and freed of the solvent to give 743 mg (69%) of 2-methoxy-9-carboxy-10,11-dihydrodibenzo[b,f]thiepin as pale reddish needles having a melting point of 185°–186° C.

IR ($\gamma_{max}^{KBr}$ cm$^{-1}$): 1690 (C=O).

NMR [(CD$_3$)$_2$SO]δ: 3.14–3.36 (2H, m, —C$\underline{H}_2$—) 3.52–3.76 (5H, m, —C$\underline{H}_2$— +OC$\underline{H}_3$) 6.54–6.75, 7.08–7.30, 7.53–7.72 (each 2H, all m, aromatic protons).

MS (m/e): 286 (M+).

EXAMPLE 61

2-fluoro-9-chloro-10,11-dihydrodibenzo[b,f]thiepin:

0.7 g of lithium aluminum hydride was suspended in 20 ml of tetrahydrofuran, to the resulting suspension was added dropwise with stirring 2.1 g of 9-chloro-11-chloro-10,11-dihydrodibenzo[b,f]thiepin dissolved in 10 ml of anhydrous tetrahydrofuran and the mixture was stirred at room temperature for 0.5 hr., further under reflux condition for 3.5 hrs., while preventing the moisture. After completion of the reaction, an excess of lithium aluminum hydride was decomposed by adding ethanol and water, and filtered off using celite. The filtrate was evaporated to obtain the residue, which was chromatographed on silica gel, eluted with chloroform, and there was obtained 1.2 g (67.0% of yield) of 2-fluoro-9-chloro-10,11-dihydrodibenzo[b,f]thiepin as pale green viscous oily substance.

NMR (CDCl$_3$)δ: 3.30 (4H, s, methylene protons due to C$_{10}$ and C$_{11}$ protons).

MS (m/e): 226, 264 (M+).

EXAMPLE 62

2-fluoro-9-cyano-10,11-dihydrodibenzo[b,f]thiepin:

The mixture of 5.5 g of 2-fluoro-9-chloro-10,11-dihydrodibenzo[b,f]thiepin, 5.4 g copper cyanide, 0.6 g of anhydrouscopper sulfate and 100 ml of N-methylpyrrolidone was refluxed overnight at 200° to 210° C. while preventing the moisture.

After cooling, to the reaction mixture was added 5 ml of conc. ammonia water and 70 ml of water, the resulting mixture was extracted with benzene, the extract was washed with water and dried over anhydrous sodium sulfate. The solvent was evaporated to obtain the residue, which was chromatographed on silica gel, eluted with chloroform, and there was obtained 1.2 g (44.4% of yield) of 2-fluoro-9-cyano-10,11-dihydrodibenzo[b,f]-thiepin as pale yellow crystals.

IR ($\gamma_{max}^{CHCl_3}$ cm$^{-1}$): 2220 (CN).

NMR (CDCl$_3$)δ: 3.40–3.63 (4H, m, methylene protons due to C$_{10}$ and C$_{11}$ protons).

M/S (m/e): 255 (M+).

EXAMPLE 63

2-fluoro-10,11-dihydrodibenzo[b,f]thiepin-9-carboxylic acid:

The mixture of 1.0 g of 2-fluoro-9-cyano-10,11-dihydrodibenzo[b,f]thiepin, 6 g of potassium hydroxide and 20 ml of 80% ethanol was refluxed with stirring overnight. After the completion of the reaction, the mixture was concentrated to obtain the residue which was dissolved in 100 ml of water. The resulting solution was extracted with diethyl ether-benzene (1:1) and the aqueous layer was acidified with conc. hydrochloric acid and extracted with ethyl acetate. The extract was washed with water and dried over anhydrous sodium sulfate. The solvent was evaporated to obtain 0.9 g of brown solid, which was recrystallized twice from benzene, and there was obtained 0.4 g (40.0% of yield) of 2-fluoro-10,11-dihydrodibenzo[b,f]thiepin-9-carboxylic acid having a melting point of 200° to 202° C. as pale brown needles.

IR ($\gamma_{max}^{KBr}$ cm$^{-1}$): 1680 (CO).

NMR [(CD$_3$)$_2$SO]δ: 3.30–3.47 (2H, m, C$_{11}$—H$_2$) 3.65–3.82 (2H, m, C$_{10}$—H$_2$) 6.98–7.92 (6H, m, aromatic protons).

MS (m/e): 274 (M$^{30}$).

What is claimed is:

1. A compound of the formula,

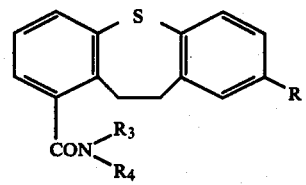

wherein R, represents a fluorine atom, or a trifluoromethyl group or 1-5 C lower alkoxy group, and R$_3$ and R$_4$ each represent a 1-4 C lower alkyl group.

2. A compound of claim 1 of the formula,

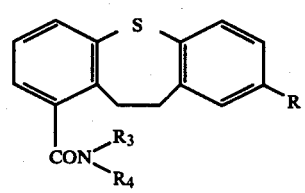

wherein R is a fluorine atom, and R$_3$ and R$_4$ are defined as in claim 1.

3. A compound of claim 1 of the formula,

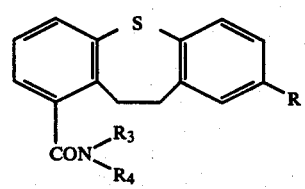

wherein R is a 1-5C lower alkoxy group, and R$_3$ and R$_4$ are defined as in claim 1.

4. A compound of claim 1 of the formula,

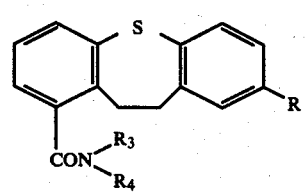

wherein R is a trifluoromethyl group, and R$_3$ and R$_4$ are defined as in claim 1.

5. A pharmaceutical composition comprising an antiinflammatorily effective amount of the compound according to claim 1 in the presence of an inert carrier.

* * * * *